(12) United States Patent
Speier et al.

(10) Patent No.: US 6,566,874 B1
(45) Date of Patent: *May 20, 2003

(54) DETECTING TOOL MOTION EFFECTS ON NUCLEAR MAGNETIC RESONANCE MEASUREMENTS

(75) Inventors: Peter Speier, Stafford, TX (US); Martin E. Poitzsch, Sugar Land, TX (US); Steven F. Crary, Sugar Land, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/356,844

(22) Filed: Jul. 19, 1999

Related U.S. Application Data

(63) Continuation-in-part of application No. 09/205,965, filed on Dec. 4, 1998.
(60) Provisional application No. 60/094,677, filed on Jul. 30, 1998.

(51) Int. Cl.[7] .................................................. G01V 3/00
(52) U.S. Cl. ......................................................... 324/303
(58) Field of Search ................................ 324/303, 306, 324/309

(56) References Cited

U.S. PATENT DOCUMENTS

| | | | |
|---|---|---|---|
| 4,350,955 A | | 9/1982 | Jackson et al. |
| 4,546,649 A | * | 10/1985 | Kantor .......................... 73/168 |
| 5,023,551 A | | 6/1991 | Kleinberg et al. |
| 5,233,302 A | * | 8/1993 | Xiang et al. ................. 324/309 |
| 5,280,243 A | | 1/1994 | Miller |
| 5,557,201 A | * | 9/1996 | Kleinberg et al. ........... 324/303 |
| 5,596,274 A | * | 1/1997 | Sezginer ...................... 324/303 |
| 5,652,513 A | * | 7/1997 | Liu et al. ..................... 324/306 |
| 5,705,927 A | * | 1/1998 | Sezginer et al. ............. 324/303 |
| 5,757,186 A | | 5/1998 | Taicher et al. |
| 6,051,973 A | * | 4/2000 | Prammer ..................... 324/303 |
| 6,297,632 B1 | * | 10/2001 | Speier ......................... 324/303 |

FOREIGN PATENT DOCUMENTS

| | | |
|---|---|---|
| WO | WO 98/29639 | 7/1998 |
| WO | WO 99/36801 | 8/1999 |

* cited by examiner

Primary Examiner—Edward Lefkowitz
Assistant Examiner—Tiffany A. Fetzner
(74) Attorney, Agent, or Firm—Kevin P. McEnaney

(57) ABSTRACT

An NMR measurement apparatus is potentially subject to relative motion between the apparatus and a sample. The measurement apparatus includes at least one magnet, at least one coil and circuitry that is coupled to the magnet(s) and coil(s). The circuitry is adapted to use the magnet(s) and coil(s) to perform at least one NMR measurement and indicate the results of the NMR measurement(s). The results are then analyzed to determine an effect of the motion on the measurement(s).

68 Claims, 20 Drawing Sheets

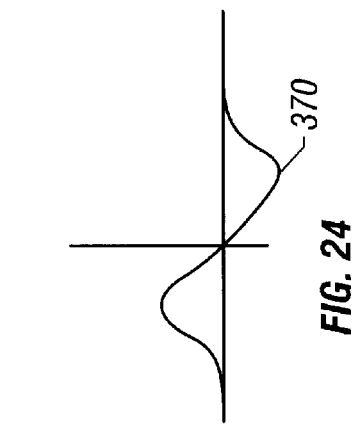
FIG. 24
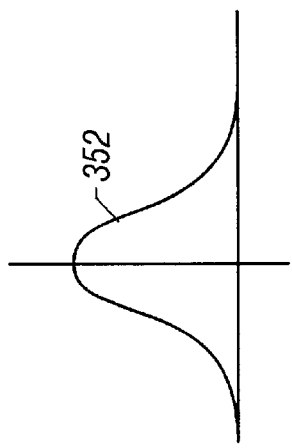
FIG. 21B
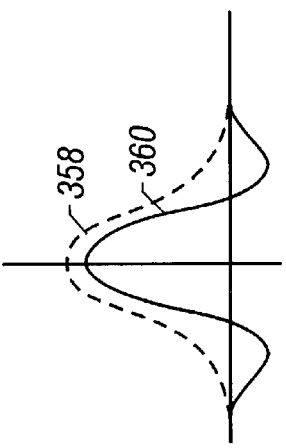
FIG. 22B
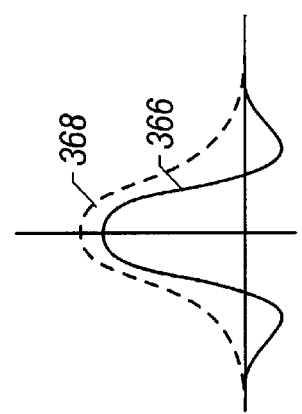
FIG. 23B
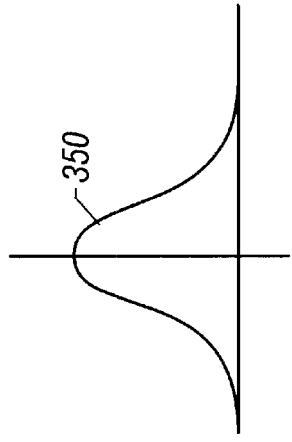
FIG. 21A
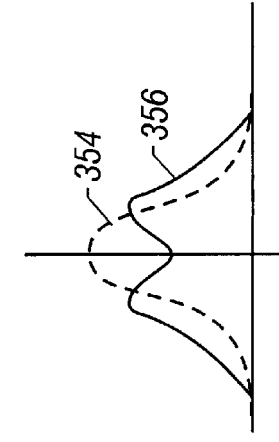
FIG. 22A
FIG. 23A

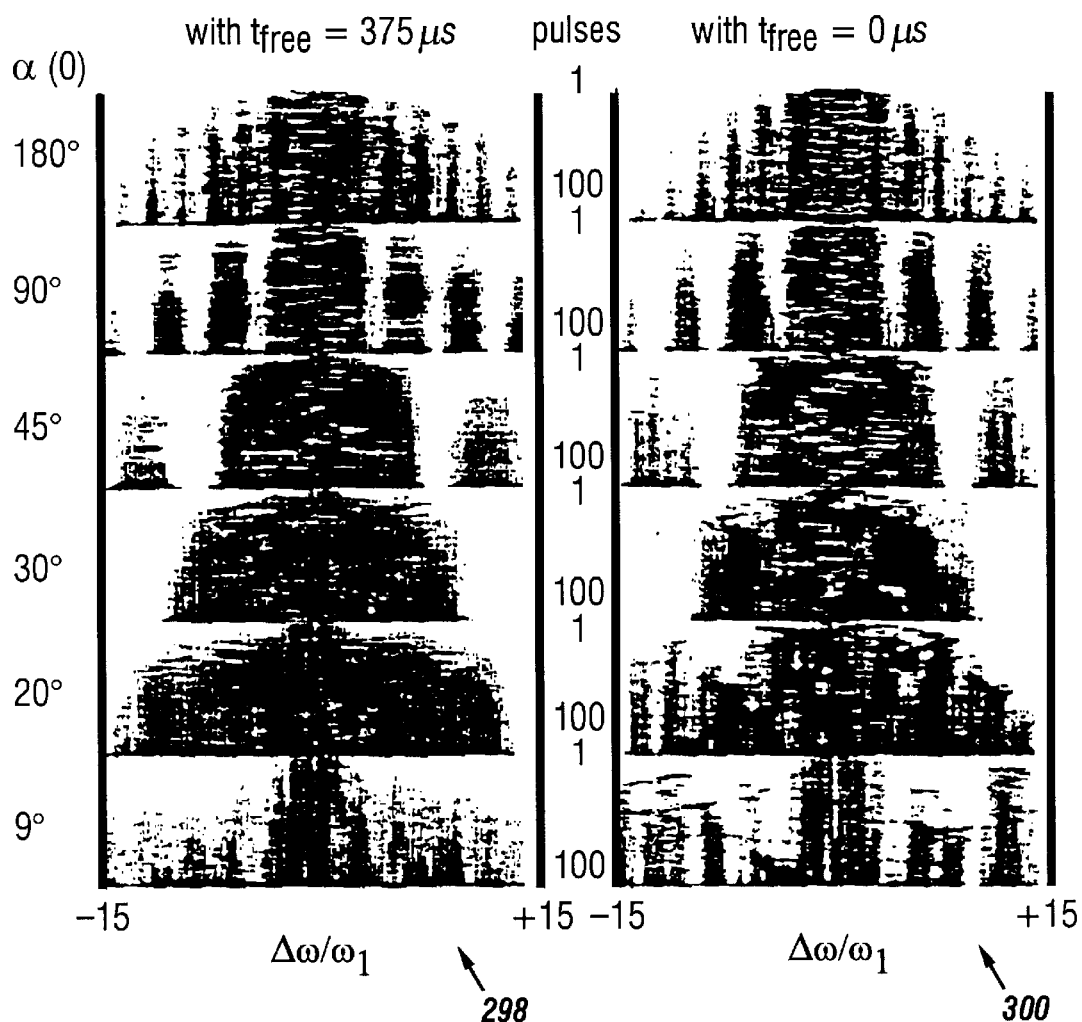
FIG. 40  FIG. 41

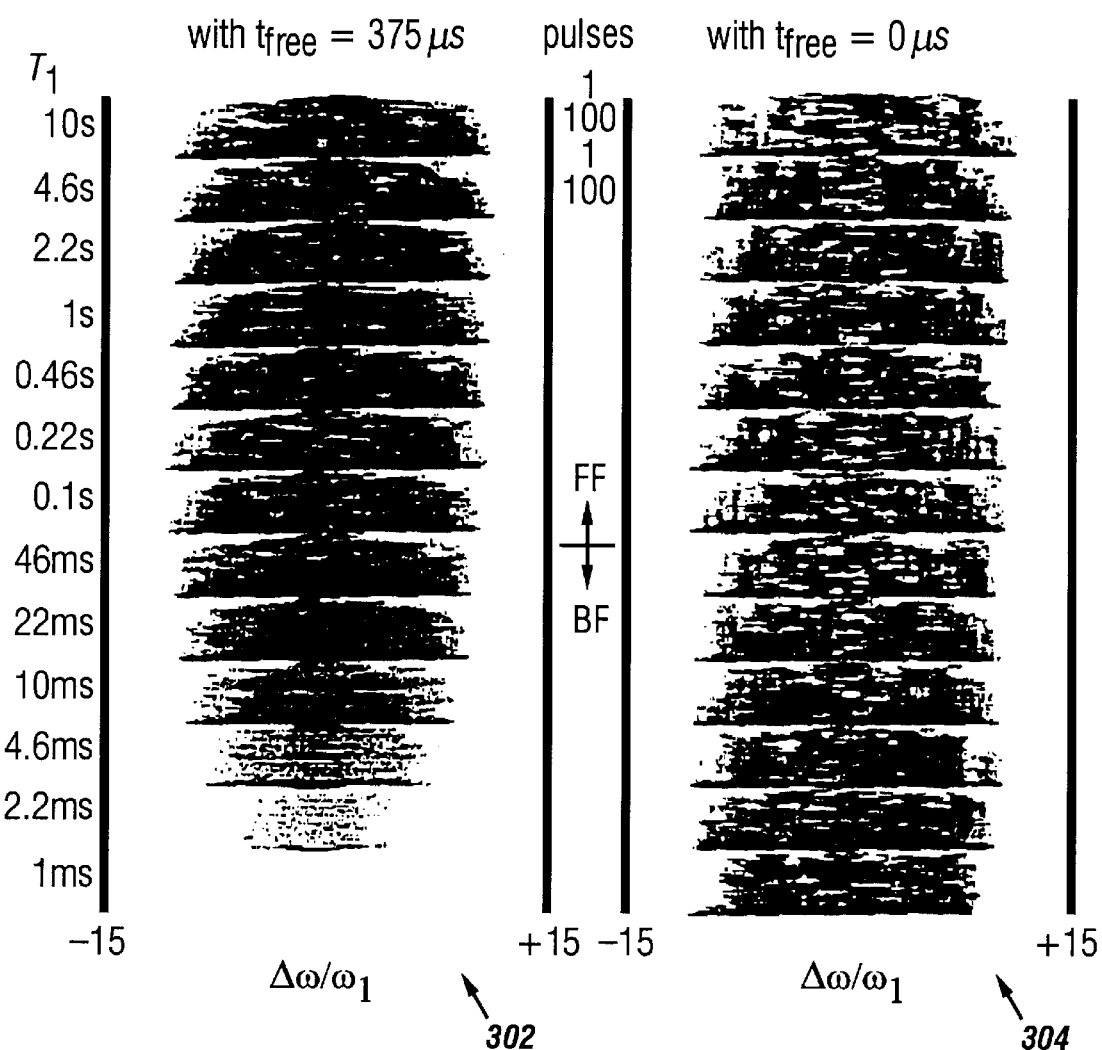
FIG. 42     FIG. 43

DETECTING TOOL MOTION EFFECTS ON NUCLEAR MAGNETIC RESONANCE MEASUREMENTS

This application claims priority under 35 U.S.C. § 119 to U.S. Provisional Patent Application Serial No. 60/094,677, filed on Jul. 30, 1998, and is a continuation-in-part to U.S. patent application Ser. No. 09/205,965, entitled, "Preconditioning Spins Near a Nuclear Magnetic Resonance Region," filed on Dec. 4, 1998.

BACKGROUND

The invention generally relates to inside-out nuclear magnetic resonance (NMR) measurements, and more particularly, the invention relates to detecting tool motion effects on NMR measurements of formation properties surrounding a borehole, such as measurements of the hydrogen content of the formation, for example.

Nuclear magnetic resonance (NMR) measurements may be used to determine properties of a sample, such as body tissue (for medical imaging purposes) or a subterranean formation (for well logging purposes). For example, for the subterranean formation, NMR measurements may be used to determine and map the porosity, formation type, permeability and oil content of the formation.

Referring to FIG. 1, as an example, NMR may be used in a logging while drilling (LWD) operation to map the properties of a subterranean formation 10. In this manner, an axisymmetric NMR tool 6 may be part of a drill string 5 that is used to drill a borehole 3 in the formation 10. The tool 6 may be, as examples, one of the tools described in Sezginer et. al., U.S. Pat. No. 5,705,927, entitled, "Pulsed Nuclear Magnetism Tool For Formation Evaluation While Drilling Including a Shortened or Truncated CPMG Sequence," granted Jan. 6, 1998; Miller, U.S. Pat. No. 5,280,243, entitled, "System For Logging a Well During the Drilling Thereof," granted Jan. 18, 1994; Taicher et. al., U.S. Pat. No. 5,757,186, entitled, "Nuclear Magnetic Resonance Well Logging Apparatus and Method Adapted for Measurement-While-Drilling," granted May 26, 1998; Jackson et. al., U.S. Pat. No. 4,350,955, entitled, "Magnetic Resonance Apparatus," granted Sep. 21, 1982; or U.S. patent application Ser. No. 09/186,950, entitled, "Apparatus and Method for Obtaining a Nuclear Magnetic Resonance Measurement While Drilling," filed on Nov. 5, 1998.

The NMR measuring process is separated by two distinct features from most other downhole formation measurements. First, the NMR signal from the formation comes from a small resonance volume, such a generally thin resonance shell, or volume 20a (see FIG. 2), and the resonance volume 20a may have a radial thickness that is proportional to the magnitude of an oscillating magnetic field and inversely proportional to the gradient of a static magnetic field. Depending on the shape of the resonance zones, the volume may extend, as an example, from as little as 1 millimeter (mm.) in one direction and as long as several inches in another. Secondly, the NMR measurement may not be instantaneous. Both of these facts combined make the NMR measurements prone to tool motions, such as the motion that is attributable to the movement of the NMR tool 6 around the periphery of the borehole 3, as further described below.

To perform the NMR measurements, the NMR tool 6 may include one or more permanent magnets to establish a static magnetic field called $B_0$; a radio frequency (RF) coil, or antenna, to radiate the time varying magnetic $B_1$ field that is perpendicular to the $B_0$ field and an RF coil, or antenna, to receive spin echoes from the formation in response to an NMR measurement, as described below. These two coils may be combined into a single transmit/receive antenna.

As an example, the NMR tool 6 may measure T2 spin-spin relaxation times of hydrogen nuclei of the formation 10 by radiating NMR detection sequences to cause the nuclei to produce spin echoes. The spin echoes, in turn, may be analyzed to produce a distribution of T2 times, and the properties of the formation may be obtained from this distribution. For example, one such NMR detection sequence is a Carr-Purcell-Meiboom-Gill (CPMG) sequence 15 that is depicted in FIG. 4. By applying the sequence 15, a distribution of T2 times may be obtained, and this distribution may be used to determine and map the properties of the formation 10.

A technique that uses CPMG sequences 15 to measure the T2 times may include the following steps. In the first step, the NMR tool 6 pulses the $B_1$ field for an appropriate time interval to apply a 90° excitation pulse 14a to rotate the spins of hydrogen nuclei that are initially aligned along the direction of the $B_0$ field. Although not shown in detail, each pulse is effectively an envelope, or burst, of a radio frequency RF carrier signal. When the spins are rotated around $B_1$ away from the direction of the $B_0$ field, the spins immediately begin to precess around $B_0$. The pulse is stopped when the spins are rotated by 90° into the plane perpendicular to the $B_0$ field. They continue to precess in this plane first in unison, then gradually losing synchronization. For step two, at a fixed time $T_{CP}$ following the excitation pulse 14a, the NMR tool 6 pulses the $B_0$ field for a longer period of time (than the excitation pulse 14a) to apply an NMR refocusing pulse 14b to rotate the precessing spins through an angle of 180° with the carrier phase shifted by ±90°. The NMR pulse 14b causes the spins to resynchronize and radiate an associated spin echo signal 16 (see FIG. 5) that peaks at a time called $T_{CP}$ after the 180° refocusing NMR pulse 14b. Step two may be repeated "k" times (where "k" is called the number of echoes and may assume a value anywhere from several to as many as several thousand, as an example) at the interval of $2 \cdot T_{CP}$. For step three, after completing the spin-echo sequence, a waiting period (usually called a wait time) is required to allow the spins to return to equilibrium along the $B_0$ field before starting the next CPMG sequence 15 to collect another set of spin echo signals. The decay of each set of spin echoes is observed and used to derive the T2 distribution.

The T2 time characterizes a time for the spins to lose irreversibly their unison precession after the application of the 90° excitation pulse 14a. In this manner, at the end of the 90° excitation pulse 14a, all the spins are pointed in a common direction that is perpendicular to the static $B_0$ field, and the spins precess at a resonance frequency called the Larmor frequency for a perfectly homogeneous $B_0$ field. The Larmor frequency $\omega_L$ may be described by the equation $\omega_L = \gamma B_0$, where $\gamma$ is the gyromagnetic ratio of the nuclei under investigation. However, the $B_0$ field is not really homogeneous, and the pulse excites spins roughly over the frequency range $|\Delta\omega| < \gamma B_1$, with $\Delta\omega = \gamma B_0 - \omega_{rf}$ being the off resonance frequency and $\omega_{rf}$ being the carrier frequency of the RF pulses. So after excitation, the spins de-phase with T2* due to inhomogeneities in the static $B_0$ field. This decay is reversible and is reversed by the refocusing pulses 14b that produce the sin echo signals. In addition, irreversible de-phasing occurs (spin-spin relaxation) and is described by the T2 time constant. This effect creates the decay of successive echo amplitudes according to the T2 time constant. Thus, typically, only spins with T2>>T2* are measured.

As stated above, the distribution of the T2 times may be used to determine the properties of the formation. For example, referring to FIG. 6, the formation may include small pores that contain bound fluid and large pores that contain free, producible fluid. A T2 separation boundary time (called $T_{SEPARATION}$ in FIG. 6) may be used to separate the T2 distribution into two parts: one part including times less than the $T_{SEPARATION}$ time that indicate bound fluids and one part including times greater than the $T_{SEPARATION}$ time that indicate free, producible fluids.

Each T2 time typically is computed by observing the decay of the magnitude of the spin echo signals 16 that are produced by a particular CPMG sequence 15. Unfortunately, the drill string 5 (see FIG. 1) may move too rapidly for the NMR tool 6 to accurately observe this decay. However, the T2 time is correlated with another time constant called a T1 spin-lattice relaxation time. The T1 time characterizes the time for the spins to return to the equilibrium direction. Considering both the T1 and T2 times, each spin may be thought of as moving back toward the equilibrium position in a very tight pitch spiral during the T1 decay. Fortunately, the T1 and T2 times are approximately proportional. As a result, the T2-based measurements may be substituted with T1-based measurements. In fact, the original work on establishing bound fluid cutoffs was done using T1. Those results were then expressed and used commercially in terms of T2.

Polarization-based measurements may use either inversion recovery sequences or saturation recovery sequences. An example of an inversion recovery sequence is described in Kleinberg et. al, U.S. Pat. No. 5,023,551, entitled, "Nuclear Magnetic Resonance Pulse Sequences For Use With Borehole Logging Tools," granted Jun. 11, 1991. Under "inside out" conditions in conjunction with motion, it may be easier to saturate a region than to invert it completely. Therefore, saturating a region may be preferred.

Referring back to FIG. 2, the T1 times typically are measured using polarization-based measurements instead of the decay-based measurements described above. In this manner, each polarization-based measurement may first include applying a saturation sequence to saturate the spins in a resonance region (such as the cylindrical resonance shell, or volume 20a. as depicted in FIG. 2, for example). Subsequently, a polarization period elapses to allow polarization of the resonance volume 20a to the field. Subsequently, a detection sequence, such as the CPMG sequence, is used to produce spin echoes from the formation 10. The amplitudes of the first few spin echo signals are then analyzed to determine an amplitude. Because only the first few echoes need to be observed to determine the amplitude of the signal, the T1 measurement may be performed in a shorter duration of time than the decay-based T2 measurement and thus, may be less prone to motion of the NMR tool 6. The detection sequence may be successively repeated (after the appropriate saturation sequence) several times with varied wait times to obtain a distribution of T1 times.

As an example, a polarization-based measurement may be used to measure the T1 times for hydrogen nuclei in the resonance volume 20a (see FIG. 2) located within the saturated volume 20b. In this manner, the NMR tool 6 may first saturate spins within the volume 20b. However, the polarization period may be sufficiently long to permit tile NMR tool 6 to significantly move within the borehole and cause the NMR tool 6 to receive spin echo signals from a shifted resonance volume 20a' (see FIG. 3) that partially overlaps the original, saturated volume 20b. As a result, tile shifted resonance volume 20a' may include a region without saturated spins (an effect typically called "moving fresh spins in") and a region of the original saturated volume 20b with saturated spins. Unfortunately, polarization-based NMR.

One way to identify potential problems caused by motion effects may be to use a motion detection device, such as a strain gauge, an ultrasonic range finder, an accelerometer or a magnetometer. In this manner, the motion detection device may be used to establish a threshold for evaluating the quality of the NMR measurement. Such an arrangement is described in PCT Application Number PCT/US97/23975, entitled, "Method for Formation Evaluation While Drilling," that was filed on Dec. 29, 1997. However, conventional motion detection devices may not specifically indicate corrections that are needed to be made to the measurement data to compensate for tool motion.

Thus, there is a continuing need for an arrangement to more precisely detect tool motion effects on NMR measurements. There is also a continuing need for an arrangement to more precisely quantify tool motion effects on NMR measurements.

SUMMARY

An NMR measurement apparatus is used to perform at least one NMR measurement of a sample. The measurements are used to determine an effect of motion between the measurement apparatus and the sample. In one embodiment of the invention, NMR measurements of the same type but with varied parameters are performed that have different sensitivities to the motion, and the results are compared to determine an effect of the motion. In another embodiment, an NMR measurement is performed to measure spin-spin relaxation times of the sample; another NMR measurement is performed to measure spin-lattice relaxation times; and the results are compared to determine an effect of the motion. In another embodiment, measurements are performed in different regions that are supposed to have different saturation thicknesses, and these measurements are used to determine an effect of the motion. In another embodiment, a characteristic of at least one spin echo signal is analyzed to determine an effect of the motion. In yet another embodiment, NMR measurements are performed in different radially adjacent regions and the results are compared to determine an effect of the motion.

Advantages and other features of the invention will become apparent from the following description, drawing and claims.

BRIEF DESCRIPTION OF THE DRAWING

FIG. 21A illustrates a spectral response for a spin echo signal that occurs in the absence of tool motion.

FIG. 21B illustrates symmetric components of a time domain response for a spin echo signal that occurs in the absence of tool motion.

FIGS. 22A and 23A illustrate symmetric components of a spectral response for spin echo signals that occur during tool motion.

FIGS. 22B and 23B illustrate symmetric components of a time domain response for spin echo signals that occur during tool motion.

FIG. 24 illustrates an anti-symmetric component of a time domain response for a spin echo signal that occurs during motion of a saddlepoint geometry tool.

FIGS. 40 and 41 are contour plots illustrating saturation in a resonance region for different numbers of pulses with and without interleaved free evolution periods.

FIGS. 42 and 43 are contour plots illustrating saturation in a resonance region for different numbers of pulses with and without interleaved free evolution periods.

DETAILED DESCRIPTION

Figure 1:
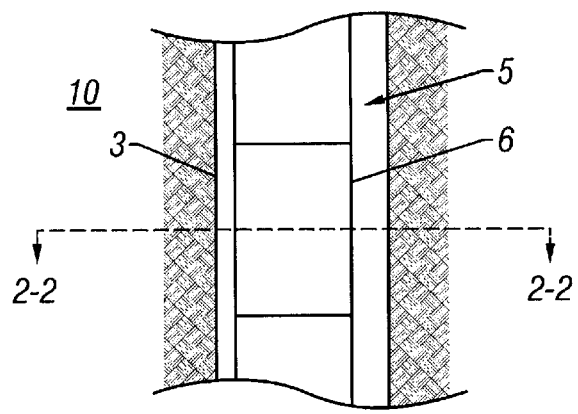
FIG. 1 is a schematic diagram of a subterranean well.
Figure 2:
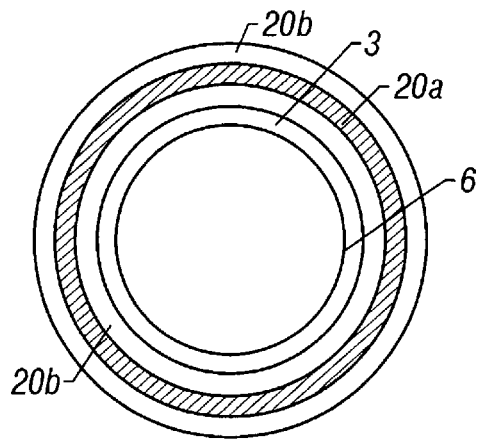
FIG. 2 is a cross-sectional view of the well taken along line 2—2 of FIG. 1.
Figure 3:
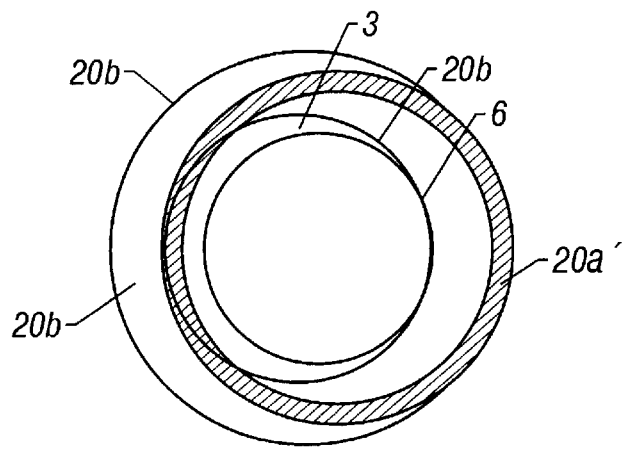
FIG. 3 is another cross-sectional view of the well after movement of the NMR tool.
Figure 4:
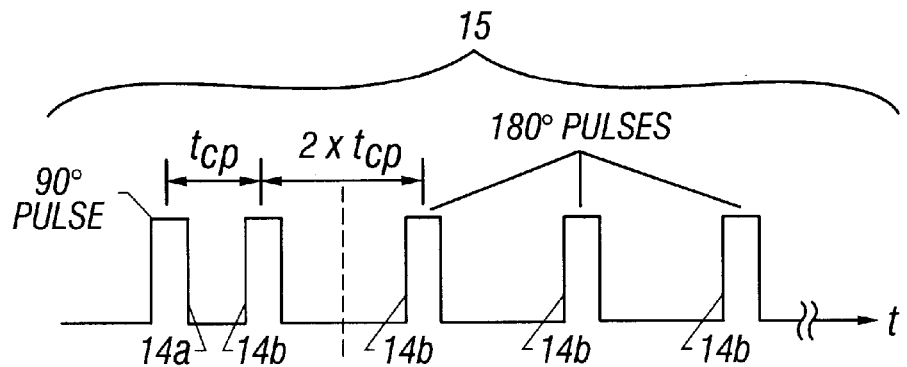
FIGS. 4 and 5 are waveforms illustrating a CPMG pulse sequence.
Figure 5:
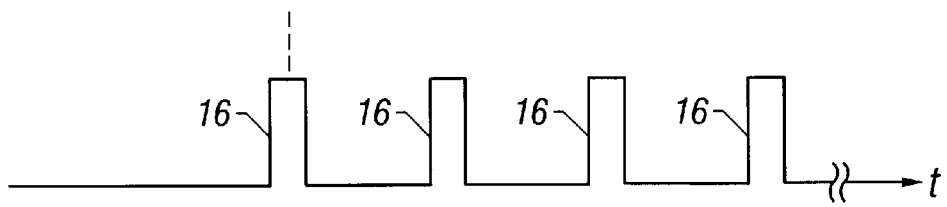
Figure 6:
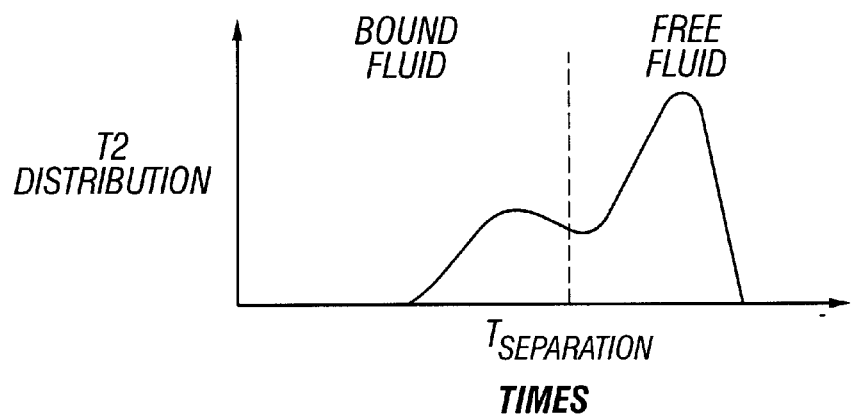
FIG. 6 is an exemplary distribution of T2 relaxation times.

An embodiment of a process in accordance with the invention detects tool motion effects during an NMR measurement by using the NMR measurement itself. In this manner, the process may include detection, characterization and/or quantification of the tool motion effects. Thus, the process may be used for quality control of the recorded data, such as determining whether a measured porosity is accurate, determining the maximum echo number at which the echo amplitudes are accurate, determining whether the entire T2 spectrum is valid, and/or determining whether a bound fluid measurement is accurate, as just a few examples. If the accuracy of the motion measurement is high enough to allow accurate quantification of the effects of the motion, the measured data may be modified to compensate for tool motion. For some embodiments where the indications of motion effects are available in real time, the measurement process may be modified to suppress motion effects.

At least five different ways are described below in which tool motion may be detected and quantified by the NMR measurement itself: 1. NMR signals from echo decay measurements that have different sensitivities may be compared to derive motion effects; 2. T1 and T2 based measurements may be compared to derive motion effects; 3. measurements may be conducted in radially adjacent resonance shells to derive motion effects; 4. the shape or frequency content of the spin echo signals may be analyzed to derive motion effects; and 5. saturation regions of different widths may be used to detect motion during polarization periods.

Some of the techniques described below permit adjustments to the measured data to compensate for tool motion. For some techniques, the necessary adjustments may be apparent from the measured data itself. However, in embodiments where the adjustments are not directly apparent from the measured NMR data, the measured data may be used in conjunction with a simulation of the spin dynamics and tool response and/or in conjunction with external information on tool motion. In this manner, the measured data may indicate displacements, and a simulation of an NMR measurement may be adjusted until the simulation results match the observed displacements. Once this occurs, adjustments to the motion data may be made based on the parameters used in the simulation. Other methods may be used for correction when the steady state motion of the tool does not change.

Although the NMR measurement techniques described below may be generally grouped together in pairs, different combinations of the techniques that are described below may be used to determine motion effects.

In some embodiments, the techniques described below may be integrated with the use of motion detection devices, such strain gauges, ultrasonic ranging devices, accelerometers and magnetometers, as examples. In this manner, in some embodiments, the motion detection device(s) may be used to detect a maximum motion threshold, a threshold at which the NMR measurement(s) may be non-correctable or unreliable. As another example, the indications of motion that are furnished by the NMR measurement(s) may be used to interpret the indications of motion that are provided by the motion detection device(s), as the motion detection device(s) may be difficult to calibrate and interpret without the additional data that is provided by the techniques described below. Other combined uses of the motion detection devices and the motion detection techniques described below are possible.

In some embodiments, motion detection device(s) may themselves be used to detect and characterize motion effects for purposes of correcting NMR measurements and checking the quality of the NMR measurements, as described below.

In the context of this application, the phrases "motion" and "tool motion" generally refer to a relative motion that occurs between the sample and the fields that are created by an NMR measurement tool. Therefore, depending on the particular embodiment, the motion may be attributable to movement of the tool, movement of the sample (where the sample is a flowing fluid, for example) or movement of both the sample and the tool.

I. Using NMR Measurements to Detect and Characterize Motion Effects

Figure 7:
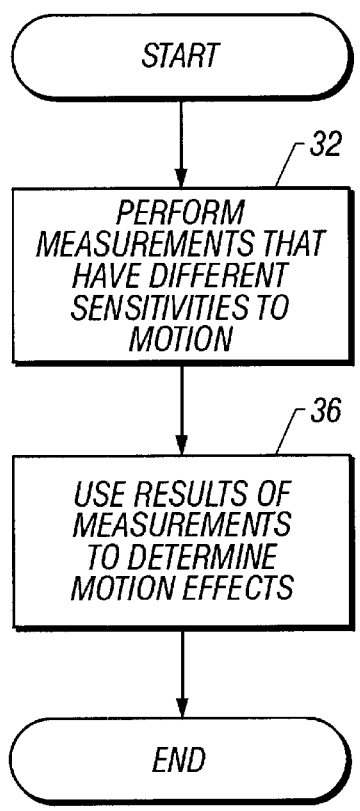
FIG. 7 is a flow chart illustrating an algorithm to determine motion effects by using different measurements that have different sensitivities to tool motion.

A. Comparison Of Different Measurements Of Echo Train Decays That Have Different Motion Sensitivities Referring to FIG. 7, one technique in accordance with the invention includes performing (block 32) NMR measurements that have different motion sensitivities and subsequently, using (block 36) the measurements to determine the motion effects. Depending on the particular embodiment, the measurements may be performed at different times and/or at spatially different locations. Because motion effects create differences in the corresponding echo trains from the different measurements, the echo trains may be analyzed to derive, for example, the highest echo number that still gives useful signal for the measurement that is least sensitive to motion.

In some embodiments, sensitivity to motion may be varied by varying the size of the resonance region by measuring in different field geometries (a saddle point geometry and gradient geometry, as an example of two different geometries) or by performing measurements with different gradients. For example, referring to FIG. 8, an NMR tool 40 in accordance with the invention is constructed to conduct two different measurements in two different locations using two different gradients. In this manner, the NMR tool 40 may include upper 44, middle 46 and lower 48 permanent magnets that circumscribe an inner protective sleeve 60 of the NMR tool 40. The upper 44 and middle 46 magnets produce a radial, axisymmetric static $B_0$ field, and the middle 46 and lower 48 magnets produce another radial, axisymmetric static $B_0$ field. Because, as an example, the upper 44 and middle 46 magnets are closer together than the middle 46 and lower 48 magnets, the upper $B_0$ field has a higher gradient (and thus, is more sensitive to motion) than the lower $B_0$ field. For convenience, the lower $B_0$ field is labeled "LG" for low gradient, and the upper $B_0$ field is labeled "HG" for high gradient in the following description.

Among the other features of the NMR tool 40, the tool 40 may include a radio frequency (RF) coil 54 to transmit $B_1$ pulses and receive spin echo signals for the upper $B_0$ field and an an RF coil 56 to transmit $B_1$ pulses and receive spin echo signals for the lower $B_0$ field. The coils 54 and 56 may be coupled to electronic circuitry 42 (of the NMR tool 40) that includes, among other things, $B_1$ pulse generators 43 and a memory 45 to store indications of the received spin echoes before transmitting indications of the spin echoes uphole.

Referring to FIGS. 8, 11, 12, and 13, the electronic circuitry 42 may be coupled to a motion device 41 (an accelerometer, strain gauge, ultrasonic finder and/or a magnetometer, as just a few examples) that indicates motion of the NMR tool. This indication may be further processed by the electronice circuitry 42 before being transmitted uphole.

Figure 8:
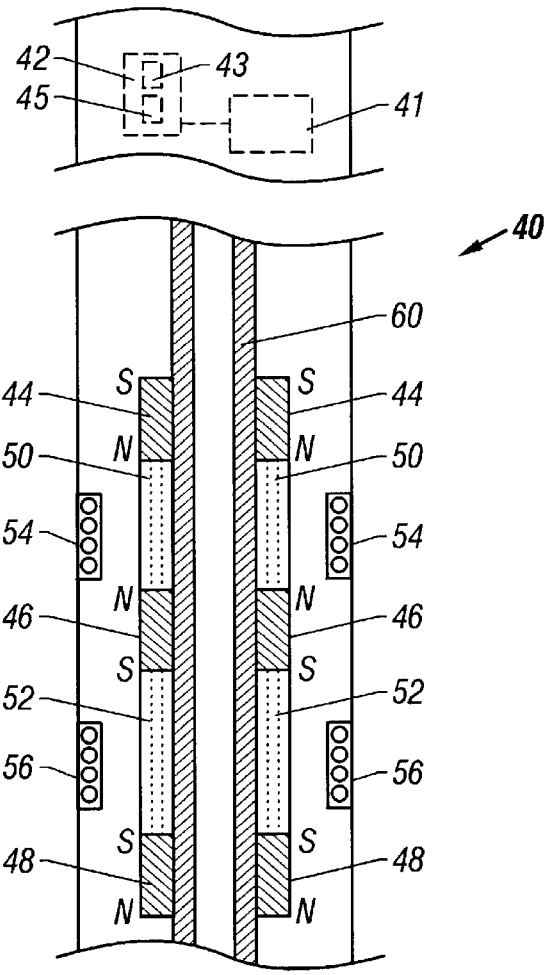
FIGS. 8, 11, 12 and 13 are schematic diagrams of NMR measurement tools.

Referring to FIG. 8, as an example, the north poles of the magnets 44 and 46 may face each other to furnish a $B_0$ field that has contour lines that extend radially away from the longitudinal axis of the NMR tool 40; and similarly, the south poles of the magnets 46 and 48 may face each other to furnish a $B_0$ field that has contour lines that extend radially into the longitudinal axis of the NMR tool 40. In some embodiments, for purposes of producing more uniform $B_0$ fields, the NMR tool 40 may include magnetically permeable sleeves 50 and 52 that circumscribe tie sleeve 60 and may be positioned between the upper 44 and middle 46 magnets and between the middle 46 and lower 48 magnets, respectively.

Figure 9:
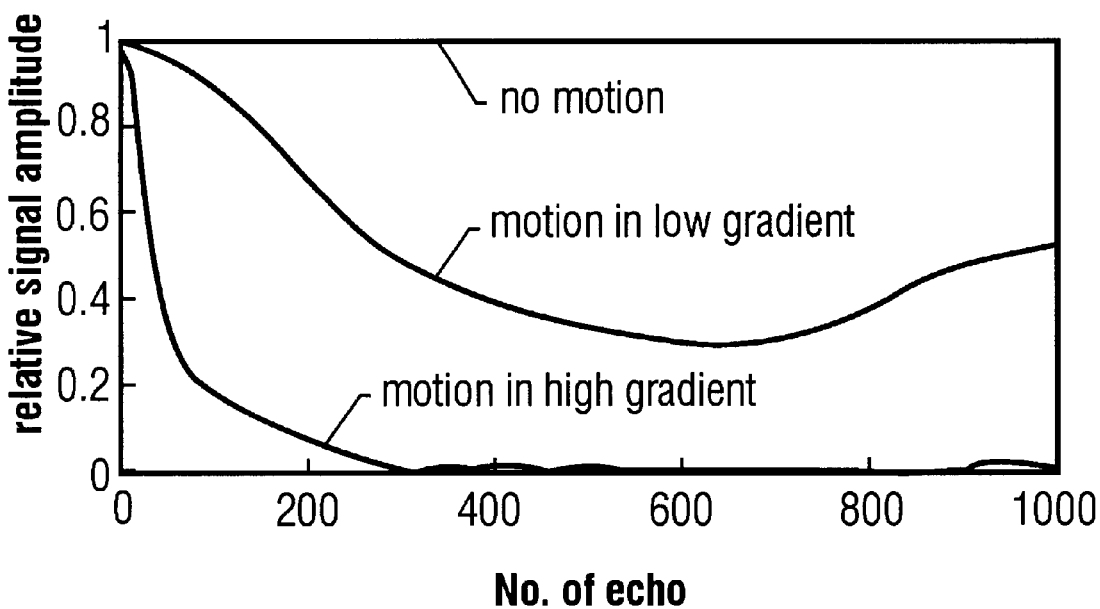
FIGS. 9 and 10 are graphs illustrating motion effects on measurements that are performed in low and high gradient magnetic fields.
Figure 10:
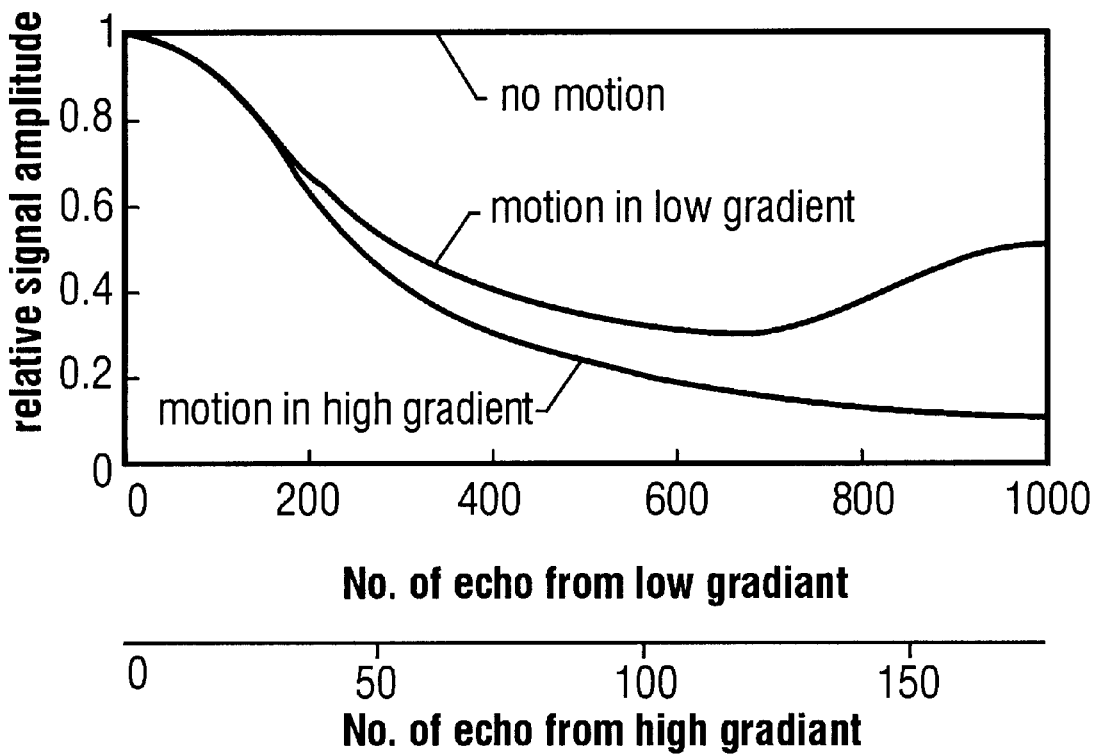

As a more specific example, the HG field may have a strength of 17 G/cm, and the LG field may have a strength of 3 G/cm. Thus, for identical pulse amplitudes, the ratio of resonance shell thicknesses is 17/3. In other words, the HG measurement is roughly six times more sensitive to motion than the LG measurement. FIG. 9 depicts an example of two simulated decays (HG and LG measurement) due to the same motion. After a certain displacement, the HG signal has been completely lost, but there is still LG signal left. Whether this signal continues to decay due to motion or not, cannot be determined from the HG signal anymore, but rather the further decay depends on the further unknown trajectory of the tool. In FIG. 10, the time base of the LG measurement is scaled with the ratio of the gradients. As shown, the initial decay curves are very similar, as expected. The deviations of the two curves after approximately echo number 200 occur because for the simulated circular motion and field geometry, the rate of change for the off resonance frequency, $$\frac{d}{dt}\Delta\omega,$$

varies with time.

Figure 11:
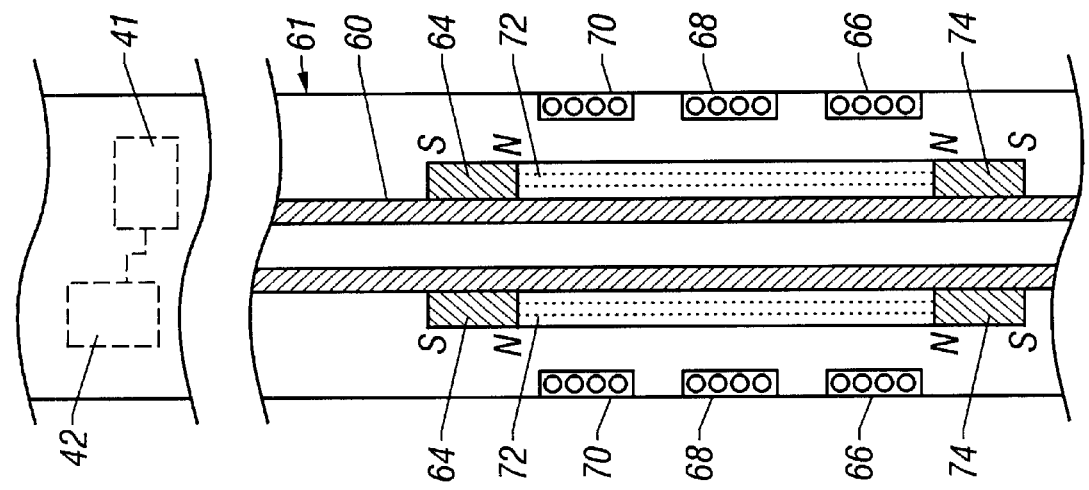

In some embodiments, two or more modular NMR tool units that each have a different motion sensitivity may be stacked together, and each of these units may establish a different field geometry, a factor that establishes a different motion sensitivity. As examples, one of the units be the tool unit 61 (depicted in FIG. 11), a tool unit 77 (depicted in FIG. 12), or a tool unit 86 (depicted in FIGS. 13 and 14). Referring to FIG. 11, the tool unit 61 may include upper 64 and lower 74 permanent magnets that circumscribe the sleeve 60. The upper 64 and lower 74 magnets cooperate with each other to provide a radial, axisymmetric $B_0$ field. The north poles of the magnets 64, 74 may face each other to furnish a $B_0$ field that has contour lines that extend radially away from the longitudinal axis of the tool unit 61. In some embodiments, a magnetically permeable member 72 may circumscribe the sleeve 60 and may be positioned between the upper 64 and lower 74 magnets. As a result of this arrangement, the magnetically permeable member 72 focuses the $B_0$ field to minimize the gradient of the $B_0$ field, and thus, produce a more uniform field. The unit 61 may or may not include the magnetically permeable member 72. More detailed descriptions of this arrangement may be found in U.S. patent application Ser. No. 09,033,965, entitled "Nuclear Magnetic Resonance Apparatus and Method For Generating an Axisymmetric Magnetic Field Having Straight Contour Lines in the Resonance Region," filed on Mar. 3, 1998; and U.S. Pat. No. 4,350,955, entitled, "Magnetic Resonance Apparatus," granted Sep. 21, 1982, both of which are hereby incorporated by reference.

The unit 61 includes gradient coils, such as coils 66, 68, and 70, that also circumscribe the sleeve 60. The coils 66, 68, and 70 may be positioned between the magnets 64 and 74 so that coils 66, 68, and 70 contribute a positive component to the $B_0$ field that may or may not be substantially aligned with the $B_0$ field, depending on the embodiment. In some embodiments, the coils 66, 68, and 70 may be formed either from a pair of single or multi-turn current loops with currents equal in magnitude and opposite in direction of circulation. For example, the coils 66, 68, and 70 may form a saddle coil.

Figure 12:
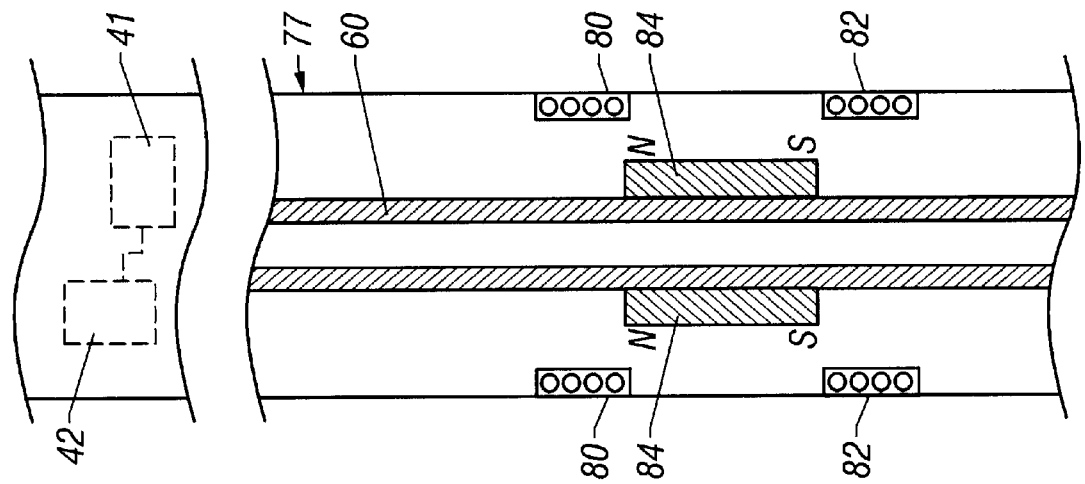

Another example of a radial, axisymmetric $B_0$ design is shown in FIG. 12, a figure that depicts the NMR tool unit 77. The tool unit 77 includes permanent magnets 64 and 74 may be replaced by an annular permanent magnet 84 that circumscribes the sleeve 60, for example, and is located between gradient coils 80 and 82. Like the magnets 64 and 74, the magnet 84 produces $B_0$ contour lines that extend radially away from the axis of the tool unit 77. As an example, the top of the magnet 84 may form the north pole of the magnetic 84, and the bottom of the magnet 84 may form the south pole.

Figure 13:
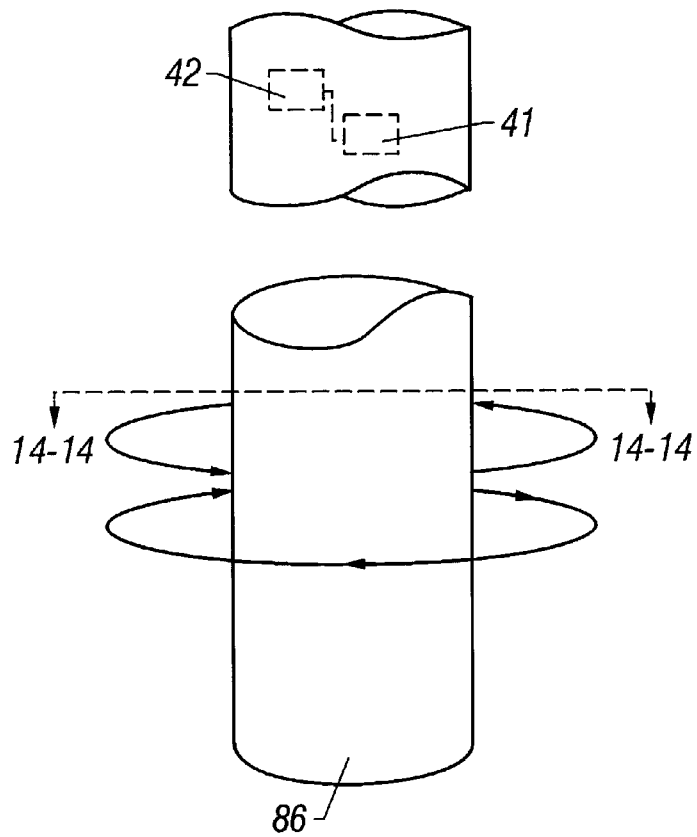
Figure 14:
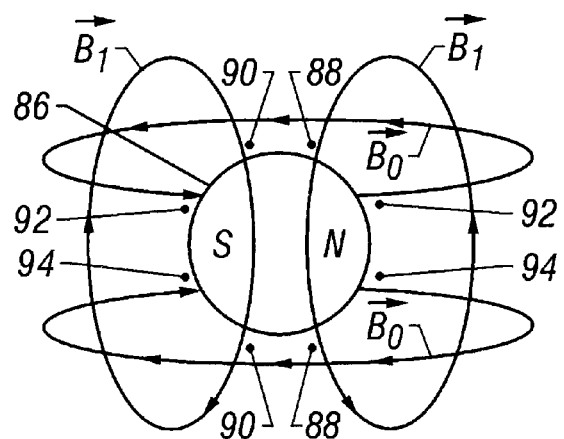
FIG. 14 is a cross-sectional view of the tool of FIG. 13 taken along lines 14—14 of FIG. 13.

An example of the tool unit 86 that produces a $B_0$ field geometry other than a radial, axisymmetric $B_0$ geometry is depicted in FIG. 13. The tool unit 86 has a two-dimensional (2-D) dipolar $B_0$ design and is further described in U.S. Pat. No. 5,280,243, entitled, "System For Logging a Well During the Drilling Thereof," granted Jan. 18, 1994, that is incorporated herein by reference. In this manner, the tool unit 86 includes an annular permanent magnet that establishes a dipole pattern for the $B_0$ field as depicted in FIGS. 13 and 14. Unlike their counterparts in the tools described above, RF coils 92 and 94 of the tool unit 86 are not concentric with the longitudinal axis of the tool unit 86, but rather, the RF coils 92 and 94 are arranged to produce a dipole pattern in the $B_0$ field so that the contour lines of the $B_0$ field are substantially perpendicular to the contour lines of the $B_0$ field in the resonance region. The tool unit 86 may include gradient coils 88 and 90 that each may include one or more rectangular loops to produce a gradient field that are aligned with the $B_0$ field that is established by the annular permanent magnet of the tool unit 86.

Other techniques beside gradients and field geometries may be used to cause different motion sensitivities. For example, the size of the resonance region affects the motion sensitivity, and it follows that the size of the resonance region may be varied by varying the $B_1$ pulse strength between measurements. For this technique, (in some embodiments) the same measurement apparatus may be used, such as one of the tools or tool units that are described above. As another example, the separation between $B_1$ pulses may be varied between measurements to change the sensitivity, as the sensitivity to motion increases generally quadratically with this separation. As another example, different pulse sequences that measure similar quantities, but have different motion sensitivity may be used. In this manner, the Carr-Purcell-Freeman-Hill (CPFH) sequence may be used for one measurement and the CPMG sequence may be used for another measurement.

As an example of another variation, the same sequence (such as the CPMG sequence) may be used for both measurements, but one sequence may be modified with respect to the other. For example, one measurement may use a standard CPMG sequence, and another measurement may used a modified CPMG sequence, such as one that includes modified pulses, non-180° refocusing pulses, different shaped pulses and/or frequency modulated pulses.

A potential drawback to the above-described techniques is that the measurements must be separated in time and/or space. In order to interpret the results it is be assumed that, in the absence of motion, the NMR signal (and therefore the formation measured) is the same in both measurements. For a continuously moving logging tool, this condition is not always given. Also the motion during the two measurements should be the same, or at least have the same characteristics. Therefore, in some embodiments, the above-described techniques may be used for quality control instead of determining quantitative motion effects. However, in other embodiments, the above-described techniques may be used for quantitative measurements, especially if such measures are taken as establishing the resonance volumes close together in space (separated radially, for example) and if the sequences are run simultaneously, either by pulsing multiple volumes at the same time or using interleaved pulsing technique.

For logging while drilling (LWD) applications, NMR lateral oscillations of the drill string may be the most important motion. As a result, the fields are chosen to be axisymmetric to allow long duration measurements while rotating. Therefore, the radial extension of the resonance region may be an important parameter for motion sensitivity.

Since the resonance regions for wireline NMR applications are designed for high logging speeds, longitudinal displacements affect wireline NMR measurements only if the displacements are very large (greater than one inch, for example). These large longitudinal displacements may be measured with other equipment, such as, by measuring the cable speed uphole. For wireline NMR, lateral motion might pose a problem only for gradient geometries because of the relatively narrow shell widths. In some embodiments, for wireline NMR, the measurements occur in radially separated shells, a technique that provides different gradients with close separation in space and no degradation of the vertical resolution of the measurement. In conjunction with adjusted pulse amplitudes different shell thicknesses (and thus, different sensitivity) may be obtained.

B. Comparison of T1 and T2 Based Measurements

Figure 15:
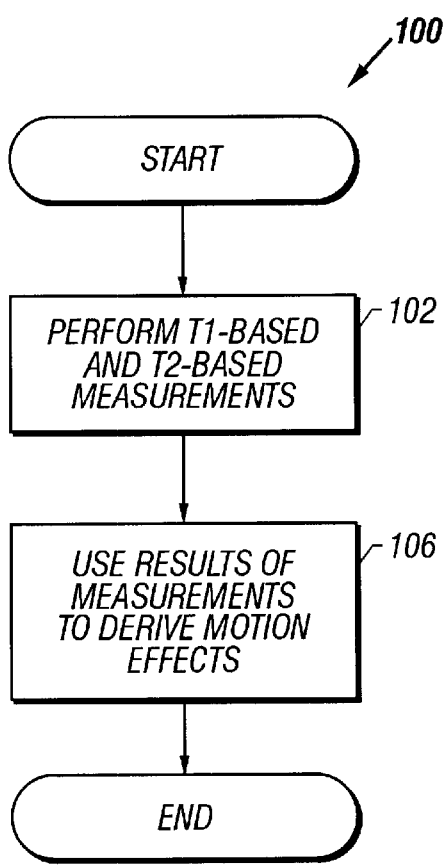
FIG. 15 is a flow chart illustrating an algorithm to derive motion effects based on T1 and T2 measurements.

In general, motion affects echo decay measurements, or T2-based measurements, more than polarization, or T1-based measurements. Therefore, motion may be characterized by comparing two measurements that measure similar quantities, but one is T1-based and the other is T2-based. In this manner, referring to FIG. 15, a process 100 that takes advantage of this observation may include performing (block 102) T1-based and T2-based NMR measurements and subsequently, comparing (block 106) the results of the measurements to derive the motion effects. The measurements do not have to be performed in a specific order, and the measurements may be performed in an interleaved fashion. One or more of the NMR measuring tools or tool units discussed above may be used to perform these measurements.

As an example, a T2-based measurement with a tapered cutoff may be performed to determine a bound fluid volume (BFV), and a T1-based partial polarization measurement may also be performed to determine the BFV. The results of the two measurements may then be compared to determine the motion effects. The partial polarization measurement relies on the magnetization in the measurement volume (that will be interrogated by the next read out sequence) being fully saturated; and full saturation may not occur if the NMR measurement tool moves during the polarization period out of the saturated region, thus introducing fresh spins into the measurement volume. However, as further described below, with as few as 40 echoes in the readout sequence, the fully saturated volume may be extended under motion to approximately four resonance shell thicknesses. In general, saturation may be optimized by using adapted "preconditioning sequences" at the end of the read out sequence, as described below.

To compare T1-based and T2-based measurements and make quantitative adjustments, the ratio T1/T2 must be approximated or known. However, if the described method is used only for quality control, the exact value of the ratio may not be important.

C. Comparison of Measurements Conducted in Adjacent Regions

Figure 16:
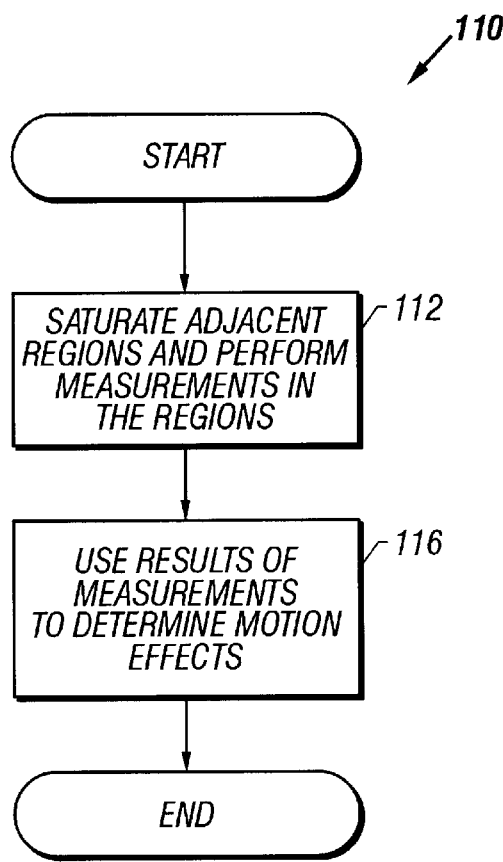
FIG. 16 is a flow chart illustrating an algorithm to derive motion effects based on NMR measurements that are performed in radially adjacent regions.

Referring to FIG. 16, another process 110 to derive motion effects may rely on the observation that tool motion that occurs during a measurement increases spin polarization losses in nearby regions beyond an expected amount (an effect described further below). As a result, the process 110 may include saturating and performing (block 112) measurements in different regions and subsequently using (block 116) the results of the measurements to determine motion effects. As an example, a T2-based measurement may be conducted in an inner first resonance shell, and thereafter, a second T2-based measurement may be conducted in an outer adjacent resonance shell. Radially adjacent shells are just one example of different regions. In other embodiments, the measurements may be conducted in other regions.

The results of the measurements may be compared to determine the motion effects. In this manner, without motion, the maximum signal loss from the measurement conducted in the outer shell should not exceed a certain amount. If so, motion may be detected and quantified, as described below. One or more of the NMR measuring tools or tools units described above may be used to perform these measurements.

More particularly, as an example, in shell I, a CPMG echo train with substantially more than five pulses (forty pulses, for example) may be applied. From this measurement the initial amplitude, i.e., for sufficiently long polarization times a porosity $\Phi_I$, may be extracted. Immediately after the last echo, the RF frequency is switched by $\Delta\omega$, and a standard CPMG echo train is recorded in a radially adjacent shell II. This echo train yields the standard echo decay constants and a initial amplitude or porosity $\Phi_{II}$. Since the two volumes are close together we expect that the formation does not change from one to the other so that we can expect $\Phi_I$ and $\Phi_{II}$ to be equal if the two measurements do not interfere with each other. In the absence of motion, the maximum signal loss in shell II does not exceed the fraction F. If $\Phi_{II}$ is not much less than $(1-F) \Phi_I$, then no significant motion on the timescale of the first echo train and on the lengthscale of a fraction of the shell thickness has taken place during the first sequence. Therefore, the results from the first sequence are trustworthy. Furthermore, the result of the second sequence is also likely to be unaffected by motion too. The echo train of shell I then provides the exact porosity and BFV. The second train of shell II provides a probably undistorted T2 distribution whose intensity is scaled with 1-F. Enhancing the signal-to-noise ratio by combining the two measurements may be questionable because of the uncertainty in F.

If $\Phi_{II}$ is much less than $(1-F) \Phi_I$, then motion on the timescale of the first echo train and on a lengthscale of at least a fraction of the shell thickness has taken place during the first sequence. So the echo decay of the first sequence might be shortened by motion and cannot be used to determine BFV. Also, the second measurement is likely to be affected by motion. Therefore, only $\Phi_I$ is reliable. The same reasoning applies, if the first pulse sequence is a long sequence (the number of pulses is much greater than 100) that potentially can detect information for a complete T2 distribution.

If in the HG/LG LWD tool design of FIG. 8, this method is applied at the high gradient and shows no motion effect, then the LG is even more likely to be unaffected by motion. If during the first measurement the saturation has not reached its plateau value, and provided that there is enough information about the T2 distribution (from previous measurements, for example), then quantitative information may be extracted about the translational motion during the first sequence.

D. Analysis Of The Spin Echo Signal Shape

Figure 17:
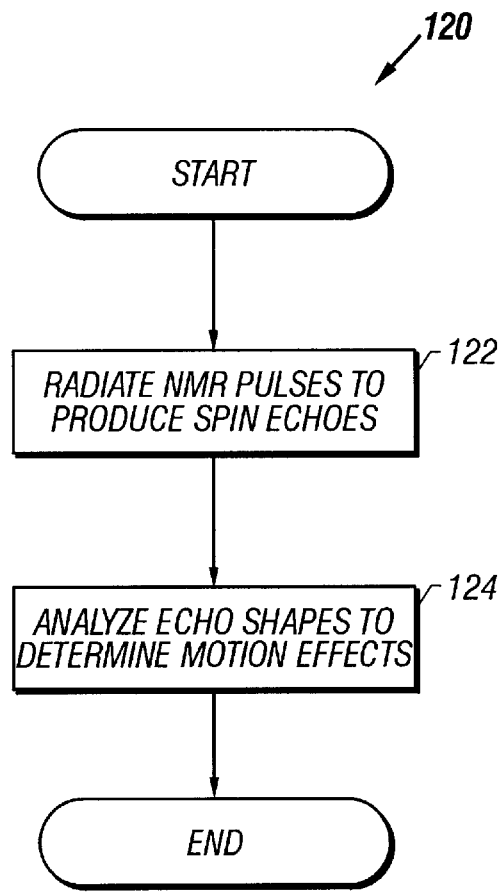
FIG. 17 is a flow chart illustrating an algorithm to determine motion effects based on shapes of spin echo signals.

Referring to FIG. 17, another process 120 to characterize tool motion effects uses the observation that the frequency contents of the spin echo signals change when the tool is moving during detection of the echo train. Thus, the process 120 includes radiating (block 122) a sequence of NMR pulses to produce spin echo signals. The spin echo signals are then analyzed (block 124) to determine motion effects.

When the tool is not moving during detection of the echo train, the shape and amplitude of the spin echo signals vary initially due to magnetization that is not aligned along the effective rotation axis from echo signal (a characteristic of each pulse sequence) to echo signal. These variations, which are predictable from known measurement parameters, die down within a few echo signals. For the rest of the sequence, the echo amplitudes decay while the spins relax, but the echo signal shape stays the same.

For the detection of an echo a substantial amount of the echo signal is digitized. The echo energy is calculated by multiplying the incoming sample vector with a filter vector and summing up the resulting vector. For optimal signal to noise the filter vector has the shape of the expected echo. If the echo deviates from this shape it will result in a reduced signal, even if the echo maximum is still the same.

Figure 18:
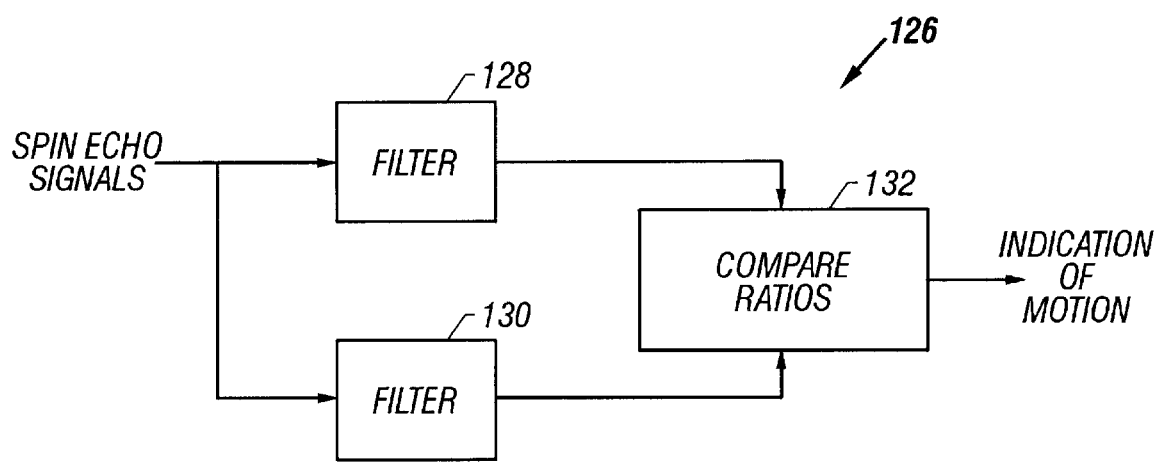
FIG. 18 is a block diagram of a system that is used to determine motion effects from spin echo signals.

FIG. 18 depicts a system 126 that may be used to indicate the effect of tool motion. The system 126 includes at least two different types of filters 128 and 130 that, as described below, may be used to detect motion of the tool. As an example, in some embodiments, the system 126 may be part of the electronic circuitry of the NMR tool. However, in other embodiments, the system 126 may be used to process logged data that is provided by the NMR tool.

Figure 19:
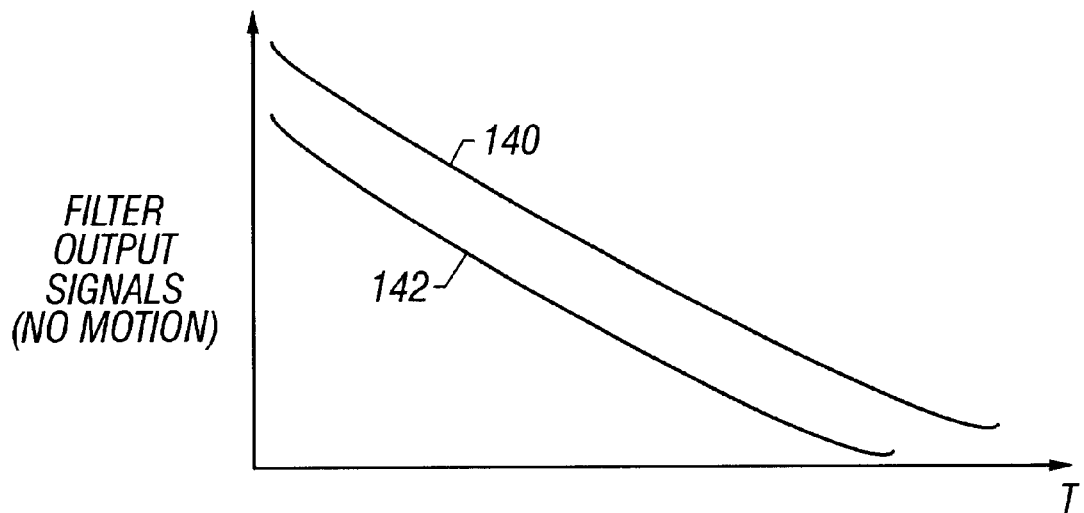
FIG. 19 illustrates filter output signals of the system of FIG. 18 for the case of motion.
Figure 20:
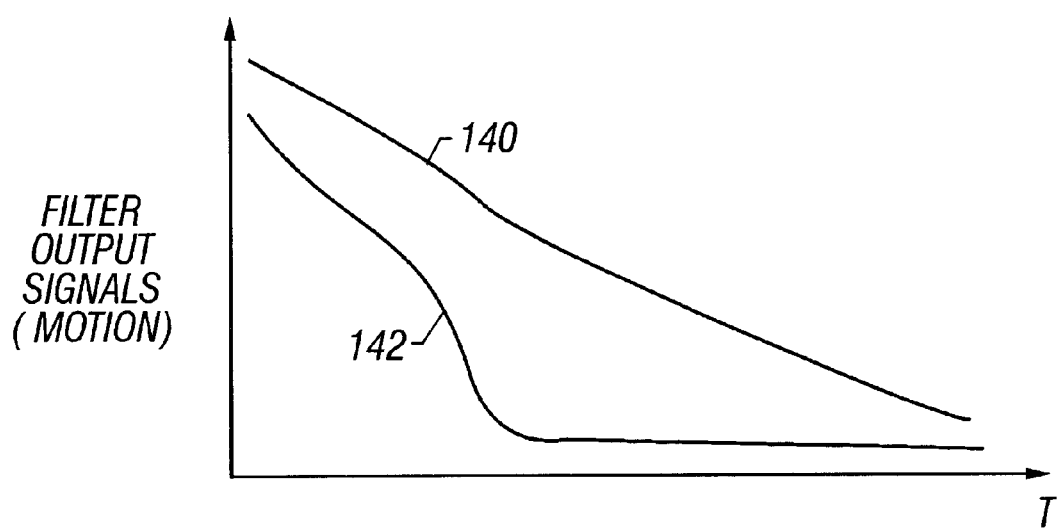
FIG. 20 illustrates filter output signals of the system of FIG. 18 for the case of no motion.

FIG. 19 shows an echo train, recorded with two different echo detection filters, in the absence of motion. Train 140 is detected with a broadband filter (filter 128, for example) while train 142 is detected with a matched, thus band-restricted filter (filter 130, for example). A simple example of a broadband filter would be zero everywhere except at the echo maximum. As depicted in FIG. 19, if no motion of the tool occurs, the decays represented by the two trains 140 and 142 are proportional to each other, However, if motion occurs, the decays are no longer proportional to each other, as depicted by the trains 140 and 142 of FIG. 20: both curves decay faster due to motion, but at different rates. The band restricted signal decays faster. Therefore, this technique includes comparing the ratios of the signals provided by the matched and broadband filters (the filters 128 and 130, as examples) to derive an indication of motion, as depicted by the block 132 in FIG. 18. Or more generally, it includes comparing the ratios of signals detected with different filters that have different motion dependencies.

The filters 128 and 130 may be several different types of filters. For example, besides the filters mentioned above, one of the filters 128 and 130 may be adapted to provide an output signal that increases with magnitude as the motion increases.

FIGS. 21A, 21B, 22A, 22B, 23A, 23B and 24 depict idealized echo shapes in the frequency and time domains in the absence of motion (see FIGS. 21A (frequency domain 350) and 21B (time domain 352)); in tile presence of motion for an axisymmetric gradient geometry (see FIGS. 22A (frequency domain 354 for no motion and frequency domain 356 for motion) and 22B (time domain 358 for no motion and time domain 360 for motion response)); and in the presence of motion for a saddle point or unidirectional gradient geometry (see FIGS. 23A (frequency domain 362 for no motion and frequency domain 364 for motion), 23B (symmetric component 368 of time domain for no motion and symmetric component 366 of time domain) and 24 (anti-symmetric component 370 of time domain for motion)).

Each echo signal is a complex vector. By phase-correcting the incoming echo signal, the resultant signal is split up into an absorptive (symmetric) real component and a dispersive (antisymmetric) imaginary component. Often (but not always), the antisymmnetric component is substantially zero and is therefore neglected. However, as depicted in FIG. 24, for motion with the saddlepoint geometry, the imaginary dispersive component 370 is not zero.

The two field geometries are different in the way the spins move in the static field in the case of tool motion: In the case of the axisymmetric gradient, for each spin that moves towards lower $B_0$, there is a spin that moves towards higher $B_0$. This results in the symmetric split of the signal in the absorptive channel and in cancellation of the signals in the dispersive channel. For a saddlepoint geometry, lateral tool motion moves spins radially away from the saddle point. No matter whether towards or away from the tool, this movement is towards lower $B_0$. Therefore, motion results in a net shift of the average signal frequency and results in a nonzero dispersive signal in the time domain.

Figure 25:
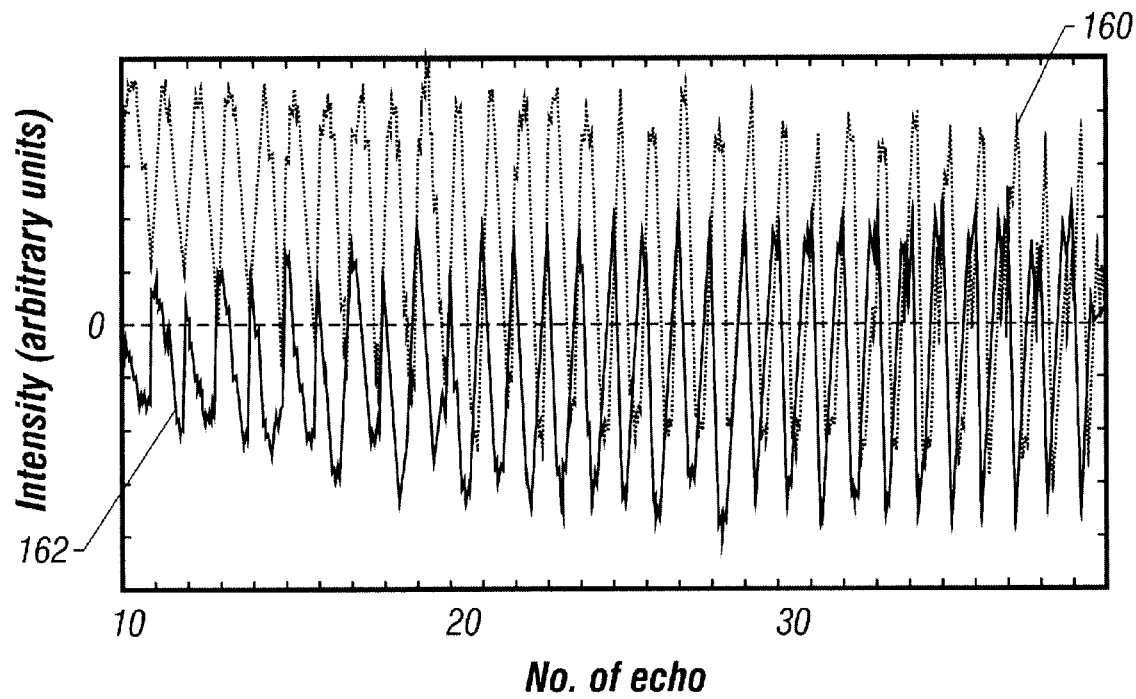
FIGS. 25, 26 and 27 are graphs illustrating received echo signals from simulated tool motion in an experimental setup.

An example of echo shape variation is depicted in FIG. 25 for the case where sawtooth shaped motion in a linear gradient was simulated. The sample was water and was inside a Hassler sized coil placed in the center of a saddlepoint of $B_0$. The motion was simulated using the following technique. During the first 50 echoes, the operating frequency $\omega_{rf}$ of the spectrometer was linearly increased. From echo 50 to echo 100 the frequency brought linearly back to the starting frequency.

As shown, for the displayed echo signals 10 to 40 the excited spins move away from resonance, generating the variations in the absorptive echo shape (represented by the graph 160). Also, the dissipative signal (represented by the graph 162) increases.

Figure 26:
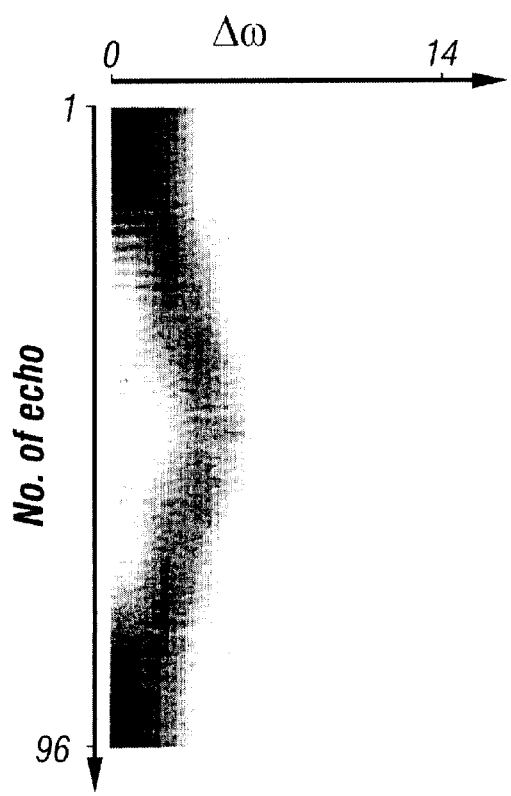
Figure 27:
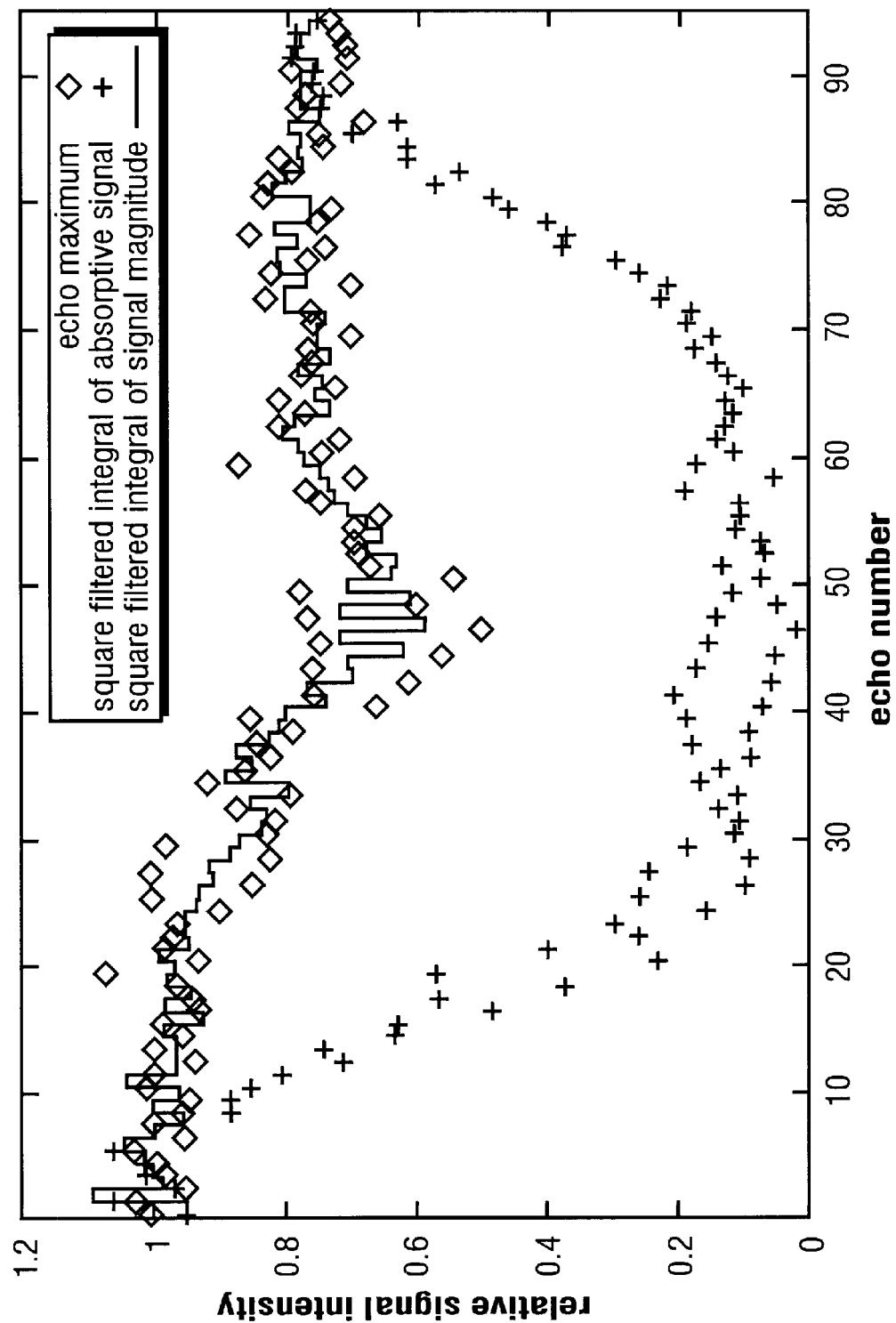

The resultant Fourier-transformed echo signals are shown in FIG. 26. The echo maximum follows the frequency variation according to the sawtooth motion. In the absence of motion, the echo amplitudes would drop to approximately 0.8 at the end of the sequence due to T2 relaxation. The result of different ways to extract the amplitude characterizing the echo is shown in FIG. 27. The diamond symbols represent the signal amplitude in the absorptive channel taken at the echo maxima. As stated above this constitutes a very broadband, but noisy detection filter. The crosses represent the (normalized) sum over all samples of the absorptive signal R, which is equivalent to applying a square filter to the time data before integration. This integral represents a crudely SN ratio optimized and narrow band filter and is more strongly affected by motion than the echo maxima. By comparing both measurements, the decay due to motion can unambiguously be detected in this case. The motion effect can then be minimized by using the noisy but less motion affected white band data instead of the narrow band signal-to-noise optimized data.

Referring to FIG. 27, the solid line shows the signal that results from summing with equal weight over the amplitudes $\sqrt{R^2+I^2}$ of the samples, where I represents the dispersive signal. Because motion was simulated by varying the spectrometer operating frequency all spins were undergoing exactly the same frequency changes. Similar to the effect of motion on saddlepoint geometries, a dissipative signal appears in this experiment. As stated above, in an axisymmetric gradient geometry, lateral motion shifts the spins on one side of the tool downfield, on the opposite site upfield, thus their dispersive signals cancel. If possible, (e.g., in saddlepoint geometries and nonaxisymmetric gradient geometries) detecting the echo in magnitude mode provides about the same (in)sensitivity to motion as taking the echo maximum. Its advantage is the superior SN ratio, the disadvantage is a nonzero noisefloor that has to be subtracted.

At least one advantage in analyzing echo shapes to determine motion is that this technique does not require additional NMR measurements (that would steal valuable measurement time). Instead, the technique is a side product that can be extracted from the NMR measurement without any compromise of the measurement itself Furthermore, as opposed to the NMR based motion measurements described herein, there is no separation in time or space between the NMR measurement and the motion measurement. Furthermore, the measurement accuracy is adapted to the effect that is measured. Therefore, this technique may be used for quantitative characterization of motion effects on NMR measurements.

To combat the problem presented by the typically small SN ratio for "inside out" NMR, two approaches may be used. The first approach is to stack the raw echo shapes and do the above analysis for the stacked echoes only. Then of course only averaged tool motion parameters may be obtained. Nevertheless it is still possible to sort out echo decay due to tool motion and T2 relaxation for purposes of deriving averaged motion parameters. For a nonaxisymmetric gradient geometry, however, the antisymmetric motion induced signal in the transverse channel however averages to zero, because its sign depends on the motion direction. Therefore, in this case the magnitude of the anti-symmetric signal should be stacked in magnitude mode. Axisymmetric saddle point geometries undergoing lateral motion, however, always create signals in the dispersive channel having the same sign.

The second approach is to sum up adjacent echoes in the echo train until the SN ratio is sufficient for the analysis. For accurate results, this technique requires that the motion is slow enough that the frequency content throughout the set of stacked echoes does not vary substantially.

E. Comparison of Measurements From Saturation Regions of Different Widths

In some embodiments, the techniques discussed above may be better suited for tool motion during the measurement up to approximately the lateral thickness of the resonance region. However, from time to time, the tool may move freely in the borehole from wall to wall and exceed the lateral thickness of the resonance region. To accommodate these larger motions, polarization, or T1-based, NMR measurements may be used, as these measurements rely on measuring signal amplitude instead of a T2 distribution. However, these methods rely on complete spin saturation. Techniques to saturate a large volume are described below in the next section. In this manner, if the tool moves out of the saturated region, incompletely saturated fresh spins move into the measurement region and distort the measurement by increasing the measured amplitude. Thus, polarization methods may be used to detect this condition and thus, to detect the tool motion.

Therefore, in some embodiments, the NMR tool (such as the tools described above) may be used to perform polarization experiments with equally effective saturation sequences and use measurements that have different motion sensitivities that are described above. For example, a high gradient (HG) field and a low gradient (LG) field may be used to measure a BFV, and then the results may be compared to determine motion effects. Using the HG and LG, motion effects may be derived for motions substantially greater than the lateral thickness of the resonance region.

Figure 28:
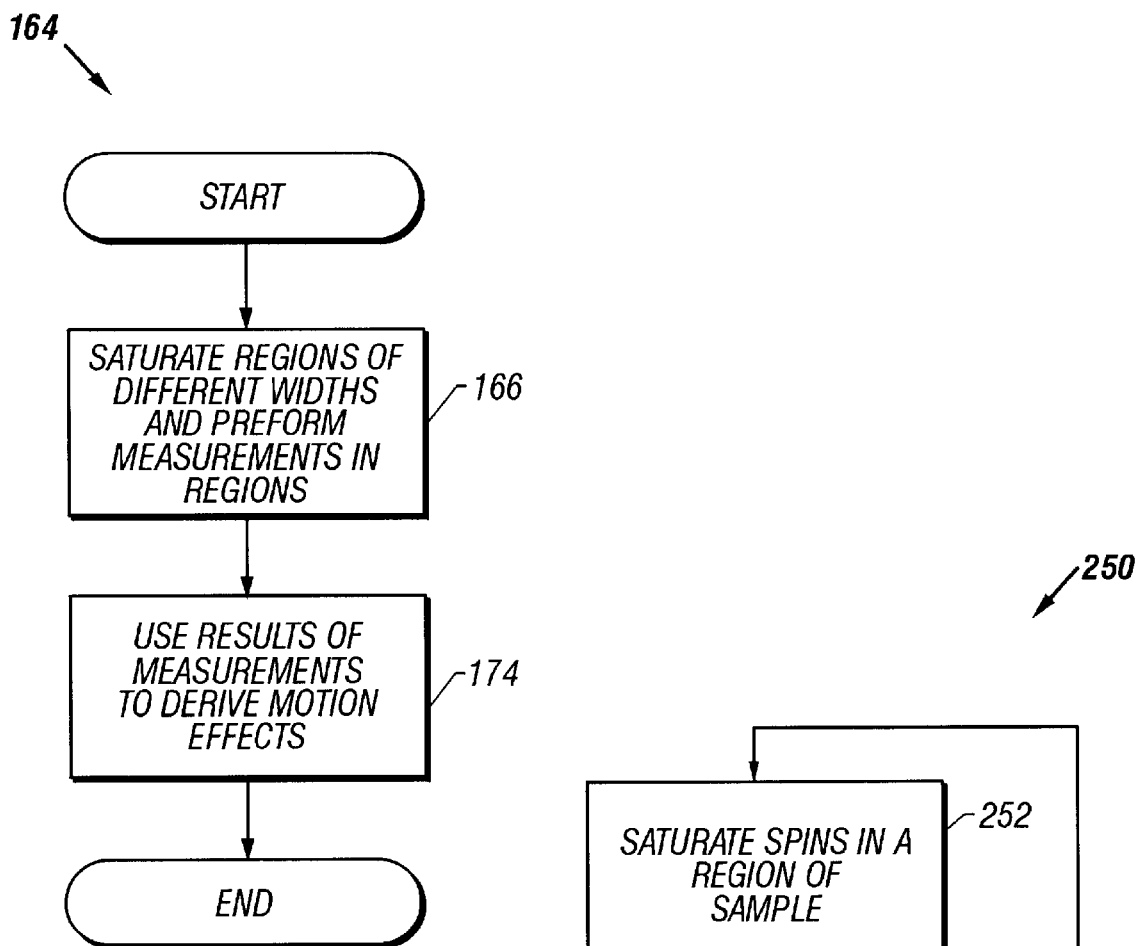
FIG. 28 is a flow chart illustrating an algorithm to determine motion effects based on the initial saturation of two different radially adjacent regions.

In some embodiments, lateral displacements during the polarization period may be detected by comparing two measurements in the same gradient that use different saturation sequences to create saturation regions of different widths. This can be achieved, for example, by using different flip angles for the saturation pulses or a number of other techniques, as described below in the description of preconditioning spins. Thus, referring to FIG. 28, a process 164 in accordance with the invention may saturate (block 166) a first region of a predetermined width. Next, the process 164 includes saturating (block 166) another region that has a different width. Measurements are performed in the first and second regions (block 166), and the results are compared (block 174) to derive the motion effects.

These comparison methods provide quality control of the measurement, but they may not allow quantitative correction of the measurement because the measurements have been taken at different times and depths, i.e., under possibly different motion conditions. Quantitative correction may be possible in the case where large displacements occur during polarization periods and negligible motion (with respect to the T2 scale) is present during echo detection. If large motion occurs, the echo train is undistorted by motion and may be checked for long T2 components. Since $T2 \leq T1$, the occurrence of T2 times that are larger than the polarization time may only be attributable to "fresh spins" that experienced long polarization times. To identify spins in which T2 is larger than the polarization time, the duration of the echo train must be comparable to or larger than the polarization time. In this manner, these spins may be removed from the analysis. Thus, this technique may be used as a quality control flag: if echo train analysis yields components with T2 greater than expected for the applied polarization period, then the initial echo amplitudes of this experiment series may not be trusted, because it contains contributions of fresh spins and only the amplitude of the low T2 components is used.

F. Preconditioning Spins a. Introduction

Figure 29:
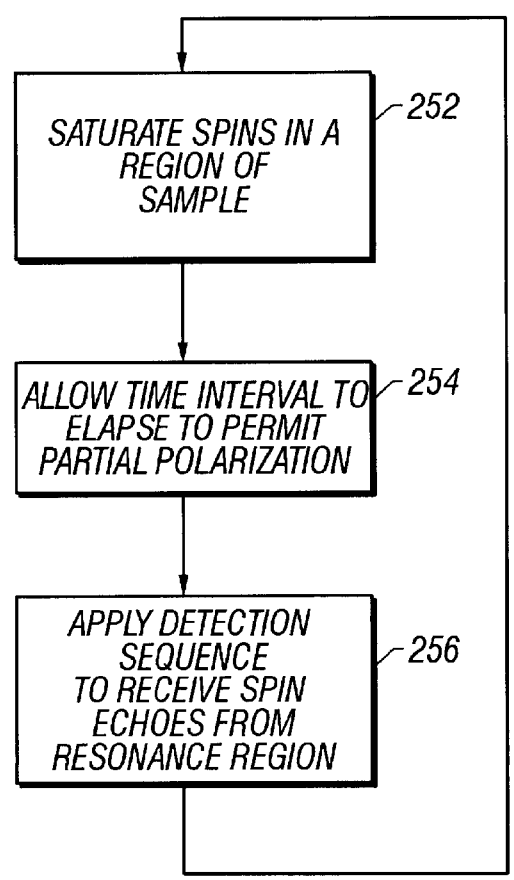
FIG. 29 is a flow diagram illustrating a polarization-based measurement according to an embodiment of the invention.

This section addresses techniques to saturate a large region for a T1-based measurement and the effects of motion on the saturated region. In this manner, referring to FIG. 29, an embodiment 250 of a process to obtain a polarization-based T1 measurement in accordance with the invention may be used by an NMR tool, such as the NMR tools and tool units described above. The process 250 includes saturating (block 252) spins in a region of a sample whose characteristics are to be measured. Next, a predetermined time interval is allowed to elapse (block 254) to allow at least partial polarization of spins in the region to occur. Subsequently, the process 250 includes applying (block 256) a detection sequence (a CPMG-based sequence, for example) to produce spin echoes from a resonance region of the sample.

In principle, each polarization-based NMR measurement includes the three building blocks 252, 254 and 256 (see FIG. 29), and one or more measurements may be used to obtain each T1 value. However, the detection sequence (i.e., the block 256) may be used to accomplish the saturation (i.e., perform the functions of block 252) and thus, eliminate the block 252 if two requirements are met: the measurements are successively repeated (called "stacked" experiments), and the signal detection sequence completely destroys the magnetization for the next measurement. If this technique is used, the results from the first measurement are discarded, as the first measurement is performed with an incorrect polarization time.

Other variations from the three basic blocks 252, 254 and 256 are also possible. As another example, the sequence block 254—block 256—block 252 may also be used to perform each measurement, and this variation may advantageous from a programming point of view. When using the second variation, the first measurement is discarded. Other variations of the process 250 are possible as long as the functions of the block 252, 254 and 256 are achieved.

The goal of the saturation, regardless of whether the saturation is being performed by an explicit saturation sequence or by a detection sequence, is to saturate a large region, or volume, with radio frequency (RF) irradiation. As described below in more detail and illustrated by simulations, depending on the particular embodiment, the saturation may be created by applying a sequence of RF pulses, such the CPMG detection sequence, that is tailored to achieve the desired saturation by slowly varying a characteristic of the sequence over time with or without motion of the NMR tool; by stochastically varying the characteristics of the sequence; or by using a combination of these techniques. The motion of the NMR tool may expand the saturation region, as further described below.

A simple CPMG sequence having constant parameters develops sharp saturated regions, called "holes," in the spin distribution. The holeburning is far reaching, but only leads to weak saturation since the holes are well separated from each other. Furthermore, once the magnetization at the positions of the holes is destroyed, continuing the sequence may not increase the saturation further. Motion of the NMR tool may increase the saturation density by "sweeping" these holes over the saturation volume, as described further below.

The CPMG detection sequence may be modified to increase the number of refocusing pulses above the typical number (ten, for example) of refocusing pulses that are necessary to measure the initial amplitude of the echo train. This method may produce a large saturated region, if motion of the NMR tool during the polarization time is always coupled with motion of the NMR tool during the detection sequence. However, less saturation may occur if the NMR tool is stationary during the detection sequence 268 but moves during the polarization time. Simulations (discussed below) show that the extent of the saturation may be enlarged by slowly changing characteristics of the sequence over time to expand the saturated region, even in the absence of tool motion, as further described below. In this context, the phrase "characteristic of the sequence" may generally refer to an envelope of the sequence or a phase of the RF carrier frequency, as examples. As examples of the possible ways to vary the envelope, the envelope may include pulses 320 (see FIG. 30) that each have a duration (called $t_p$), and the pulses 320 may be spaced apart (from center to center) by time intervals called $t_e$. In this manner, the $t_p$ duration and/or the $t_e$ time interval (as examples) may be varied to expand the saturated region, as further described below.

The characteristics of the detection sequence (i.e., the sequence used for purposes of saturation) may be varied not only slowly but also in an uncorrelated, or stochastic, manner from pulse to pulse, as further described below. The stochastic extremum is the irradiation of incoherent noise. The stochastic variation of the characteristics is to be contrasted to the slow variation of the characteristics in which the saturation affects are far reaching because the coherent, non-stochastic characteristics of the sequence dominate. As a result, slow variation of the characteristics may result in far off resonance holes being incrementally burned by consecutive pulses. However, the stochastic variations cause consecutive pulses of the sequence to not contribute to the same hole. As a result, the stochastic variation of the pulses generally provides a more consistent saturation density. As described below (and illustrated by simulations), these two techniques may be combined to enhance both the scope and density pattern of the saturation. As also described below, if motion is present that is fast enough to sweep holes over the distance that separates adjacent holes during only a few pulses, the coherent element of the sequences is destroyed, and a sequence with slowly varied characteristics may perform similarly to a sequence with stochastically varied characteristics.

As described below, the flip angles of the refocusing pulses in the CPMG sequence may not need to be large to create off-resonance saturation if coupled with some other variation (variation of the phase of the carrier frequency, for example). Therefore, by shortening the RF pulses, the power necessary for saturation may be decreased. For sufficiently short pulses, the influence of the hole burning is negligible. This being the case, the free evolution period between pulses may be dropped, and saturation may be achieved in much shorter time. In the limit of very short pulses, this technique results in irradiation of incoherent noise whose frequency spectrum can be designed to fit the needs. In practice, the finite rise and fall times of the pulses set the lower limit of the pulse duration. There may be a tradeoff to be made between time and power necessary to achieve saturation and saturation bandwidth, as described below.

b. Saturation Using a CPMG Sequence

In the following, an example of a saturation using a CPMG sequence with and without slow motion induced changes in $\vec{\omega}_0$ is discussed in detail. Although this description specifically refers to a CPMG sequence, the above-described hole burning may be accomplished by all multi-pulse sequences that feature a large number of repetitions of a building block of pulses, as an example.

The repeated coherent pulsing during a CPMG sequence excites selected spins with $\Delta\omega >> \omega_1$ where $\omega_1$ is approximately equal to the radial thickness of the resonance volume.

The excitation steps become smaller and smaller with increasing $\Delta\omega$, but the excitations sum up from pulse to pulse, in the holes for significant amounts. Because the transverse magnetization decays in accordance with T2, the selected spins become "saturated." The separation (called $\Delta\omega_h$) of these holes is determined by the periodicity of the sequence. Nonnegligible pulse duration and off resonance effects cause some deviation, so the $\Delta\omega_h$ separation of the holes is approximately described by the following:

$$\Delta\omega_h = \frac{2\pi}{t_e},$$

where $t_e$ is the echo spacing from the beginning of one refocusing pulse to the beginning of the next refocusing pulse.

Coupled with relaxation, the simple CPMG sequence technique results in hole burning at certain off resonance frequencies. It may not be possible to measure in between the burned holes, because the width $\Delta\omega_s$ of the measurement region extends over $\Delta\omega_s \approx 2\omega_1$, which for 180° refocusing pulses of duration $t_p$ becomes $\Delta\omega_s \approx 2\pi/t_p$. Since $t_e$ is always greater than $t_p$, $\Delta\omega_s > \Delta\omega_h$ and there may be several holes burned into a resonance region. To calculate the extent of the signal loss, the field geometries, the relaxation times and the detection bandwidth must be taken into account.

Figure 31:
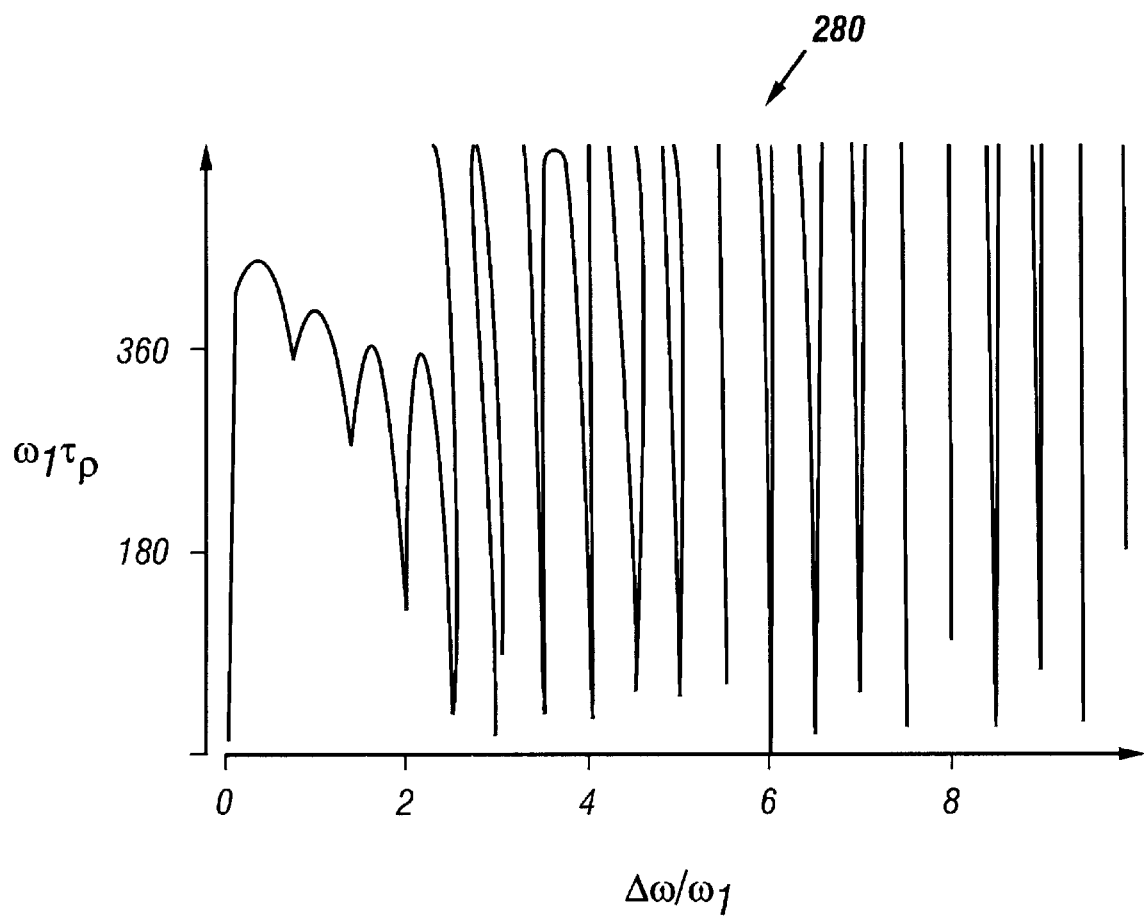
FIGS. 31, 34, 36 and 38 are contour plots showing saturation in a resonance region.

To illustrate the distribution of holes, FIG. 31 is a two-dimensional contour plot 280 (derived from a simulation) showing a calculated contour plot of the distribution of holes burned into a longitudinal magnetization of $M_z=1$ with linear variation in $\omega_0$ on the horizontal axis and $t_p$ on the vertical axis. The white areas represent full conservation of magnetization, and the black areas represent reduction from 100% saturation, or inverted magnetization. The first CPMG sequence is applied at $\Delta\omega=0$, and shown is the effect on the off resonance magnetization $M_z$ immediately after the end of this CPMG sequence. The parameters of the sequence of CPMG pulses are $t_e=500$ $\mu$s, $t_{p180}=125$ $\mu$s, where k is the number of refocusing pulses=1000. The relaxation times are chosen to be long, but a fraction of the duration of the echo train. In this simulation, perfectly rectangular pulses were used. However, embodiments of the invention may use substantially rectangular pulses and may use substantially non-rectangular pulses. In FIG. 31, the effect of the first excitation pulse was not simulated.

Figure 32:
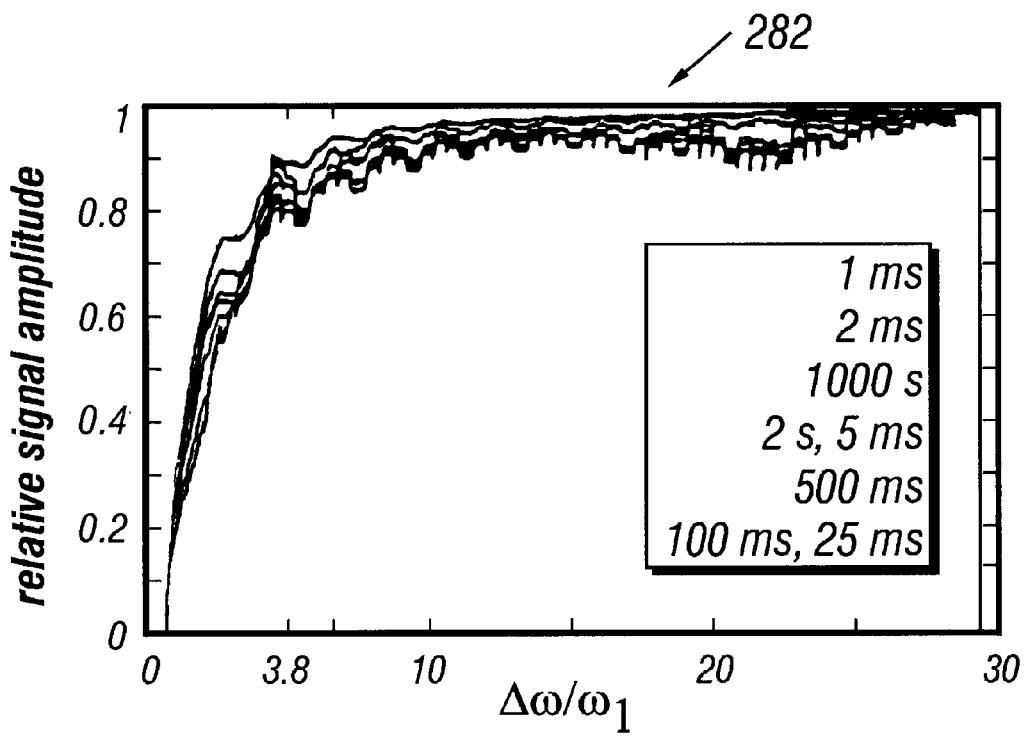
FIGS. 32, 33, 35, 37 and 39 are plots of relative signal amplitudes received from a region surrounding the NMR tool, illustrating saturation.

FIG. 32 shows for several relaxation times, the simulated resultant relative signal amplitudes 282 (i.e., $M_z/M_\infty$) that are available to a second measurement at the frequency shifted by the abscissa $\Delta\omega$, that is reduced by saturation from a first measurement (as described above) for $\omega_1 t_p = \pi$, when averaging $\Delta\omega=\pm0.75$ $\omega_1$. This means that the $\omega_0$ frequency of the carrier has been shifted by $\Delta\omega$ between measurements. The relative signal amplitudes 282 are each associated with a different T1 time (approximately equal to 2*T2, as an example). The parameters for the second measurement were the same as for the first measurement and the flip angle of the pulses was chosen to be 180°. In the figures (and in the simulation), it was assumed that $$\frac{d\omega_1}{d\omega_0} = 0,$$

i.e, in an axisymmetric $B_0$ and $B_1$ gradient geometry, the $B_0$ field does not change in the neighborhood of the resonance region. For this case, the horizontal scale ($\Delta\omega/\omega_1$) is proportional to the difference in radiuses (of the resonance region) between the first and second measurements. Also, the assumption that $\omega_1$ is a constant is a valid approximation when the difference in radiuses is much smaller than the radius, a fact that justifies the choice of a constant flipangle in the plot.

Figure 33:
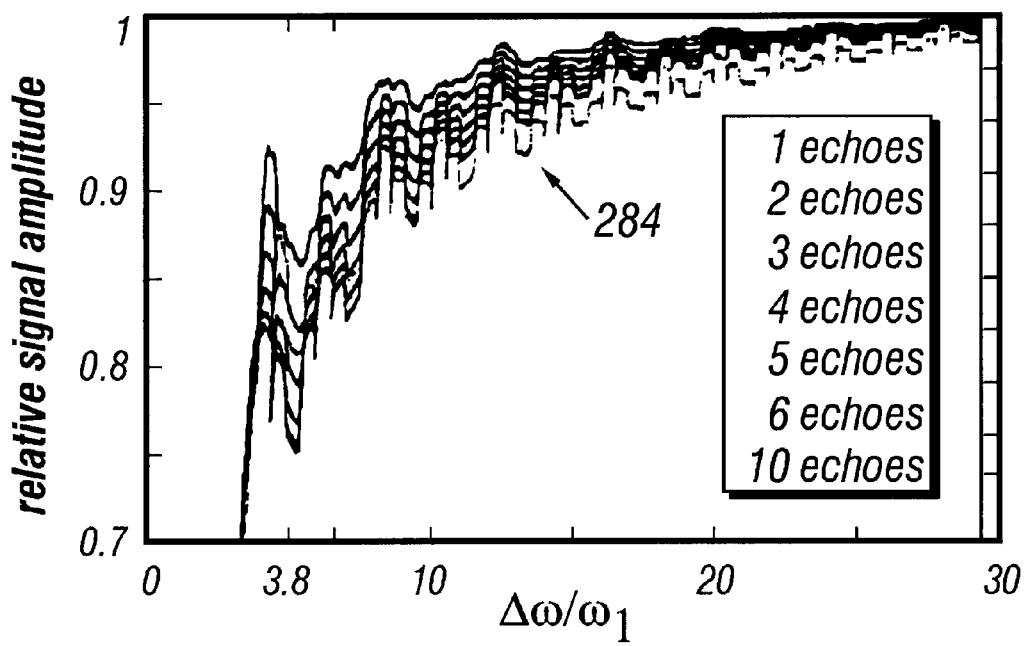

As can be seen from FIG. 32, the saturated region basically extends not further than $2\cdot\Delta\omega/\omega_1$, that is twice the radial thickness of the resonance region. The next measurement starts only with complete saturation, if the resonance region is radially shifted less than $1\cdot\Delta\omega/\omega_1$. FIG. 33 shows relative signal amplitudes 284 that are each associated with a number of refocusing pulses in the first sequence. As can be seen, most of the saturation at smaller $\Delta\omega$ occurs within the first ten echoes. Here and in the following examples, T1=2·T2=100 msec. was chosen.

Figure 34:
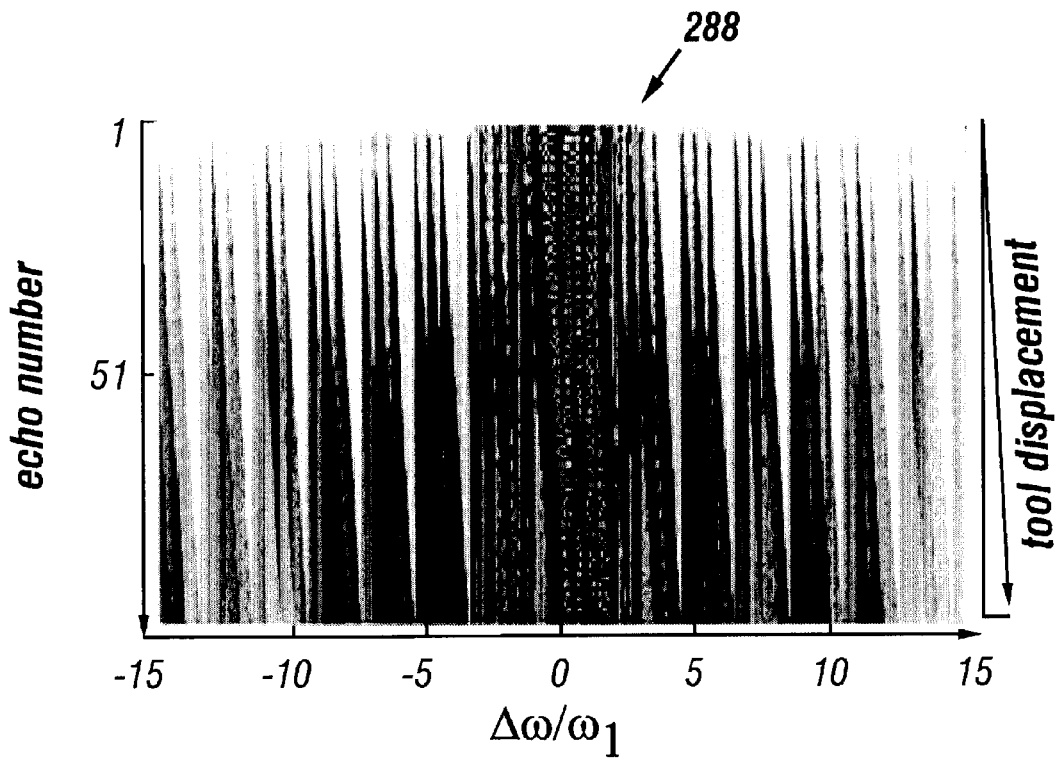

Tool motion during the first CPMG sequence may result in an increased loss in nearby resonance regions. For example, FIG. 34 shows a contour plot 286 of the development of the off resonance $M_z$ magnetization during the first sequence for a translation speed of the tool of $-20\omega_1/s$. The horizontal axis denotes the off resonance frequency $\Delta\omega$ over $\omega_1$ (pulse amplitude) of the first CPMG sequence. The contours describe the relative longitudinal magnetization left after the first CPMG sequence. The amplitude of the pulses are assumed to be constant. The pulse parameters and relaxation times are the same as above. The vertical axis indicates how many refocusing pulses were applied in the first CPMG sequence with carrier $\omega_{RF}$, which is approximately proportional to the duration of this sequence. The number k of refocusing pulses ranges from one refocusing pulse (i.e., a block spanning approximately 500 s) for the top plot to 100 refocusing pulses (i.e., a block spanning approximately 50 ms) for the bottom plot. In this example, during 50 ms, the NMR tool travels the distance of $+1\omega_1$, which is roughly half a shell width. In the beginning, carrier $\omega_{RF}$ corresponds to $\Delta\omega=0$, at the end, carrier $\omega_{RF}$ corresponds to $\Delta\omega=+1\cdot\omega_1$. As shown, with increasing relaxation times and/or echoes, the translation of the NMR tool "sweeps" the holes over the spin distribution and thus, increases the density of the saturation.

Figure 35:
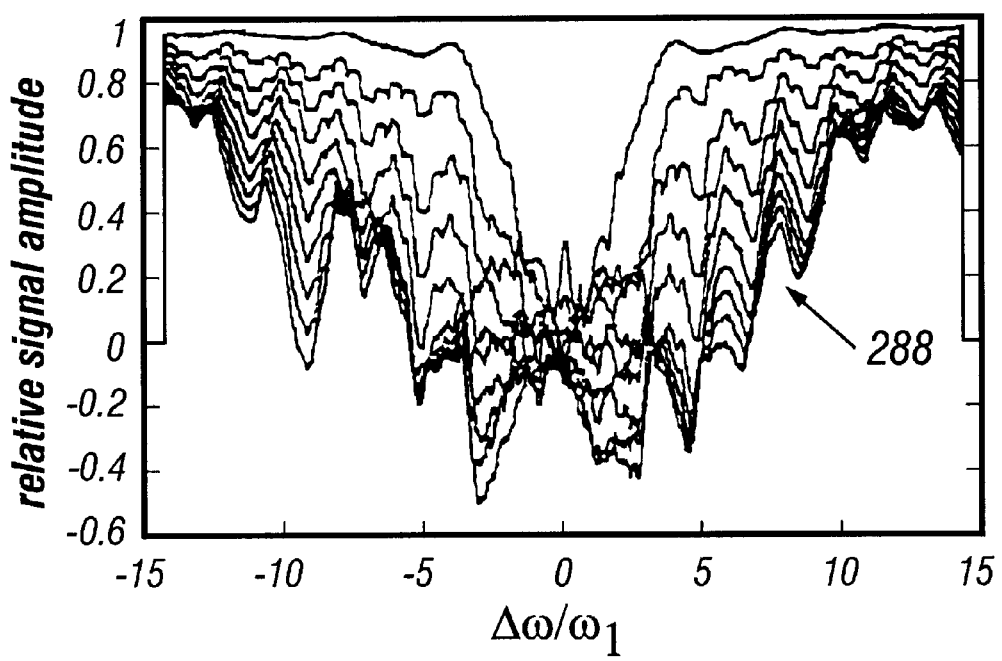

The resulting relative signal amplitudes (i.e., $M_z/M_\infty$) 288, when averaging over a (rectangular, for purposes of the simulation) shell of width $\pm 0.75\omega_1$ is shown in FIG. 35. From top to bottom, the amplitudes 288 represent the result for k=1, 11, 21, 31, 41, 51, 61, 71, 81, 91. Note that the loss increases with echo number and for more than 10 echoes becomes much stronger than the saturation effect without motion of the NMR tool, as shown in FIGS. 32 and 35. The saturated region has now a width of more than $5\omega_1$. The loss increases for a time comparable to the relaxation times of the spin and can even lead to negative signal for small $\Delta\omega$. The exact profile depends on the motion and on the relaxation times of the spin ensemble. The profile gets narrower for smaller relaxation times.

It is assumed above that the pulses in the CPMG sequences are perfectly rectangular pulses. However, real "rectangular" pulses may never reach this ideal but may be subject to finite rise and fall times. This limits the width of the frequency spectrum contained in the pulses. At far off resonance, the width of the burned holes and the speed of burning them is proportional to the amplitude of the frequency component of the pulse at the position of the hole. Therefore, in some embodiments, far off resonance hole burning may be less effective than in the simulations described above. In some embodiments, non-rectangular pulses may be intentionally used.

For the pulses discussed in this application, a wide frequency distribution may be beneficial. Therefore, in some embodiments, rectangular pulses with the shortest possible rise and decay time constants may be preferred. Furthermore, the saturation region can be optimized by varying the shape of the pulse envelope to adapt the frequency content of the pulse.

In general, far reaching saturation in the absence of motion may be created by irradiating a repetitive multipulse sequence with slowly varying parameters and broadband pulses. If the pulse sequence parameters are slowly varied while the sequence is applied, the positions of the burned holes move slowly over the spin distribution and increase the saturation. Varied pulse sequence parameters include:

variation of the echo spacing $t_e$, variations of $t_p$, variations of $\vec{\omega}_1$ by, as examples, pulse amplitude, field direction and carrier frequency, $\omega_{RF}$, variation of $\vec{\omega}_0$, and variation of the pulse phase.

Variations of combinations of these parameters and variations of other parameters are also possible. Variations in $\vec{\omega}_0$ and $\vec{\omega}_1$ may be caused by actual variations of the $B_0$ and $B_1$ fields (e.g., variation of magnet spacing and rf power) or by relative motion of sample and the NMR tool. In this manner, relative motion of the sample with respect to the NMR tool may stem from motion of the sample (e.g., fluid flow or diffusion) or from tool motion.

Another way to vary $\vec{\omega}_0$ is to vary the static field with the help of an electromagnet, or "gradient coil", such as the gradient coils of the NMR tool 40 (see FIG. 8) the tool unit 61 (see FIG. 11), the tool unit 77 (see FIG. 12) or the tool unit 86 (see FIGS. 13 and 14), as just a few examples. Therefore, as a result of the above-described arrangements, the spins precess around $\vec{\omega}_0+\vec{\omega}_0^{gradient}$. The largest effect occurs if both vectors are parallel. Thus, as a result of this technique, $\Delta\omega$ may be varied without varying $\omega_{rf}$. This may be advantageous to varying $\omega_{rf}$ because the bandwidth of an antenna with high quality factor limits the range of possible variation for $\omega_{rf}$ (without returning which is unpractical during a saturation sequence at least if it is done by switching capacitors using mechanical switches). In some embodiments, a drawback of this method may be the relatively large amount of energy needed for driving the electromagnet (compared to the use as an imaging device) since it must be fired with varying amplitudes throughout the saturation sequence. There are several ways to use the gradient coil (or coils):

Constant current is established in the gradient coil throughout one pulse (of the $B_1$ field) to effectively shift the radius of the resonance region for this pulse.

The current in the gradient coil is varied throughout one pulse (of the $B_1$ field) to create a "sweep" pulse without varying the frequency of the rf pulse. Depending on the actual parameters, the sweep pulse may invert, excite or saturate a particular region.

The gradient coil is fired between the pulses (of the $B_1$ field) to destroy possibly conserved transverse magnetization. If the gradient pulse duration (called $t_{grad}$) is so short that the variation of the flip angle $\alpha=\omega_0^{gradient} t_{grad}$ over the saturated region is negligible, this is similar to stochastically varying the phase of the pulses of the $B_1$ field.

The current in the gradient coil may be pulsed concurrently with each pulse of the $B_1$ field, and, as an example, this technique may be used in an inversion recovery sequence (instead of a saturation sequence) to invert a large region around the NMR tool.

The gradient coil may be used to create the stochastic or continuous variations described above. Other uses of the gradient coil(s) are possible.

c. CPMG Sequence With Stochastic Variations

Figure 36:
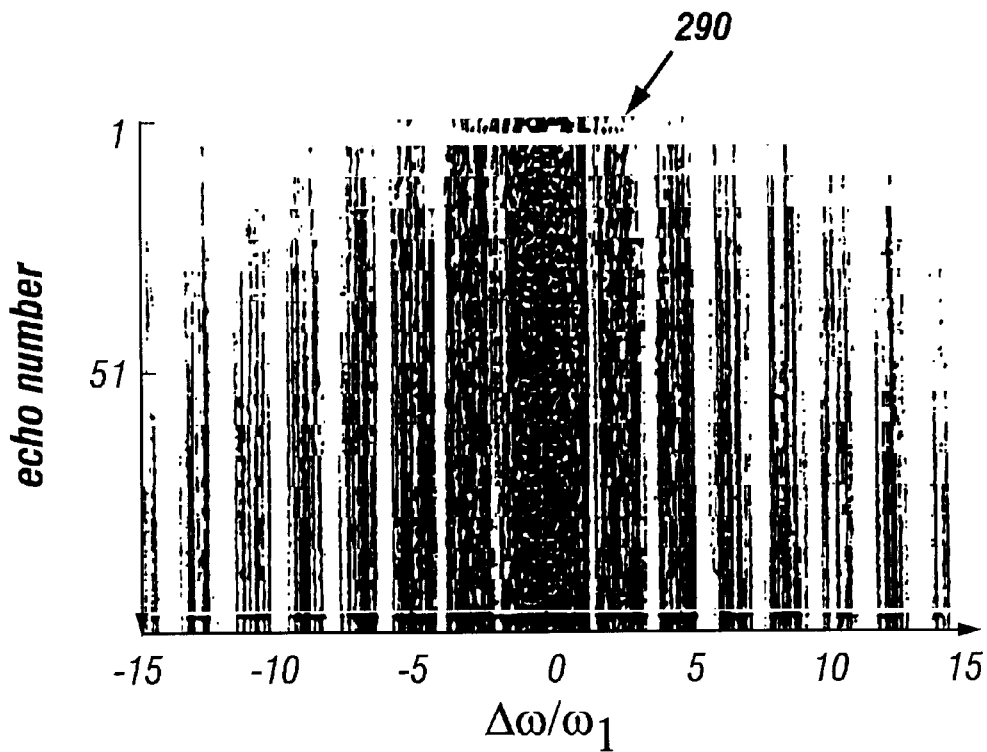
Figure 37:
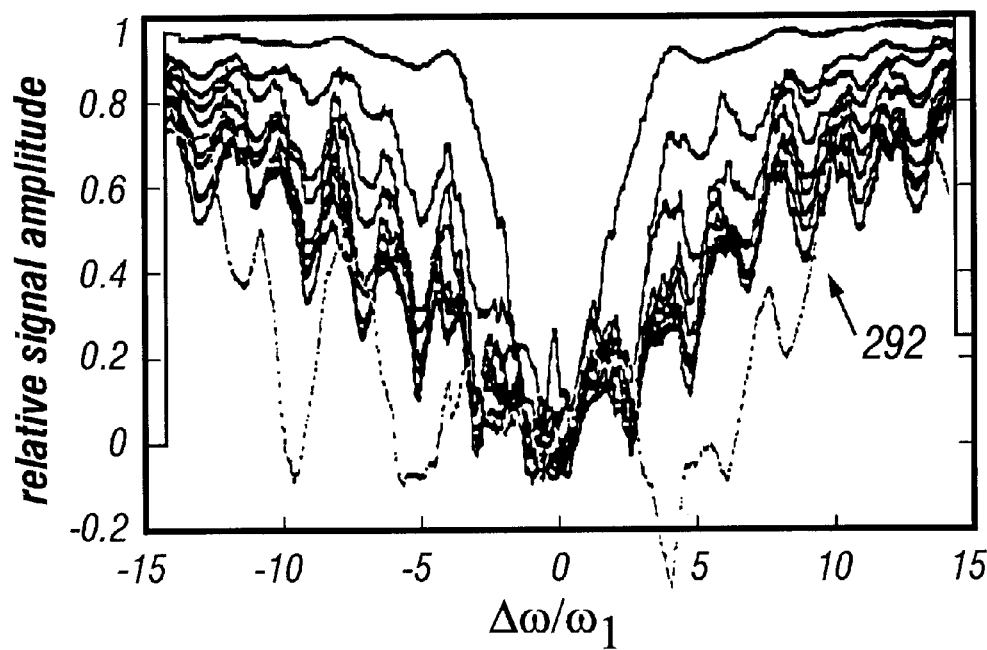

The pulse train characteristics of the CPMG sequence may also be stochastically varied. For example, the $t_p$ duration of each pulse may be randomly varied to randomly create 0°, 90°, 180° and 270° pulse phases (at least three pulse phases are available in typical NMR spectrometers), as examples. Referring to FIG. 36 (showing a contour plot 290 of relative signal losses for different echo numbers) and FIG. 37 (showing a contour plot 292 of relative signal losses for different echo numbers when averaged over a radial volume thickness of $\pm 0.75\omega_1$), an example is shown where the pulses are randomly generated, and the NMR tool does not move. Except for this randomization of the pulse phases, all spin and pulse parameters are the same as in the examples described above.

As can be seen, the saturation bums wide and well separated stripes into the spin distribution. The width of the saturated region is smaller than the width of the region created by the motion influenced CPMG sequence, but the saturation profile is much smoother than the one created with a CPMG sequence. This indicates a tradeoff between the extent of the resonance region (using coherent features) and reliable quantitative saturation profile (using stochastic features). It should be noted that the profiles created by a CPMG sequence get a smoother shape for spins with $T_{1,2}$ (100 ms, as an example)$<<t_m$ (50 ms, as an example), where $t_m$ is the duration of the CPMG sequence. The occurrence of motion during application of the random phase sequence slightly increases its performance, and the profile stays smooth.

Figure 38:
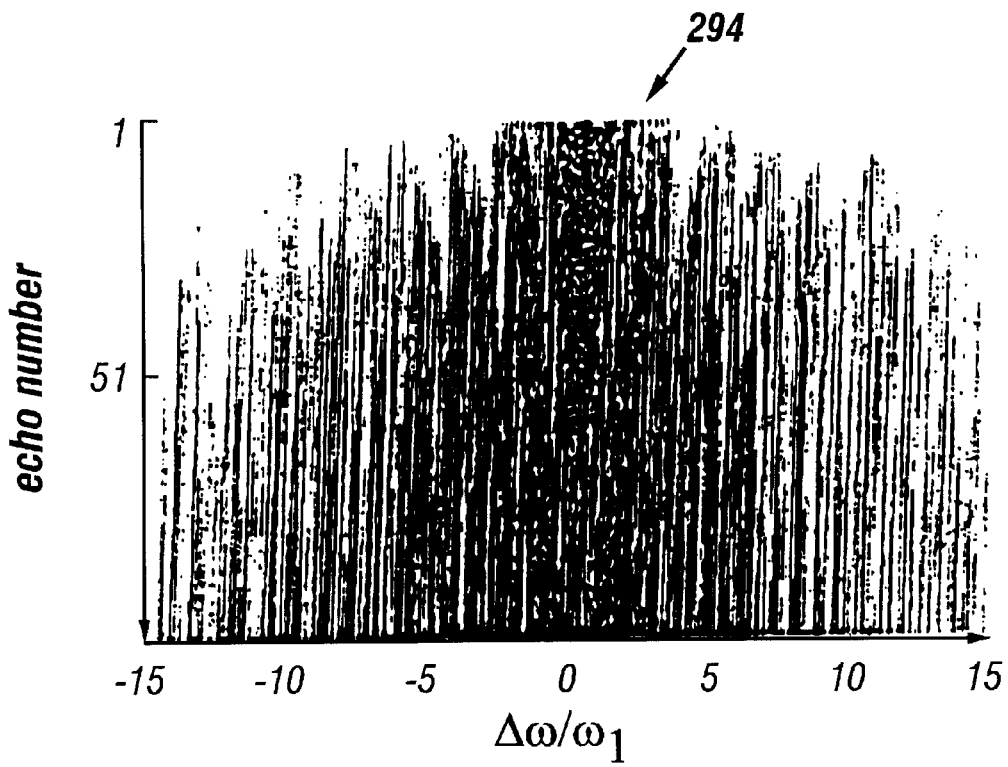

The stripes of incomplete saturation occur because not every hole is burned with the same "speed." Depending on the position $\Delta\omega$, some holes may even be completely suppressed as can be seen, as an example, in FIG. 38 where every fourth hole is missing. The position of these insufficiently saturated spots depends on the duration of the refocusing pulse: Off resonance, a pulse of duration $t_p$ rotates a spin through the angle $$\alpha(\Delta\omega) = \sqrt{\omega_1^2 + \Delta\omega^2}\, t_p$$

around its "effective rotation axis" that points in the direction $\vec{\omega}_1 + \vec{\Delta}\omega$. The unsaturated "nodes" appear where $\alpha$ is a multiple of $2\pi$. Therefore, by varying $\omega_1 \cdot t_p$, these spots may also be saturated.

Figure 30:
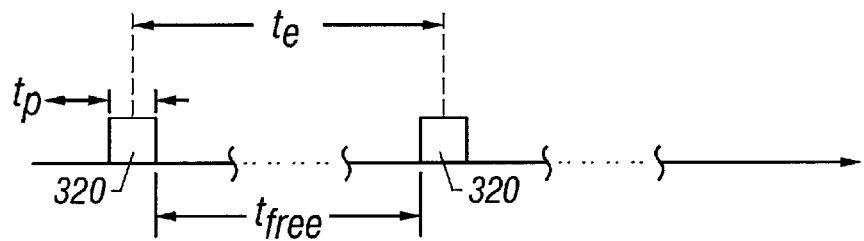
FIG. 30 is a waveform illustrating an NMR pulse sequence.
Figure 39:
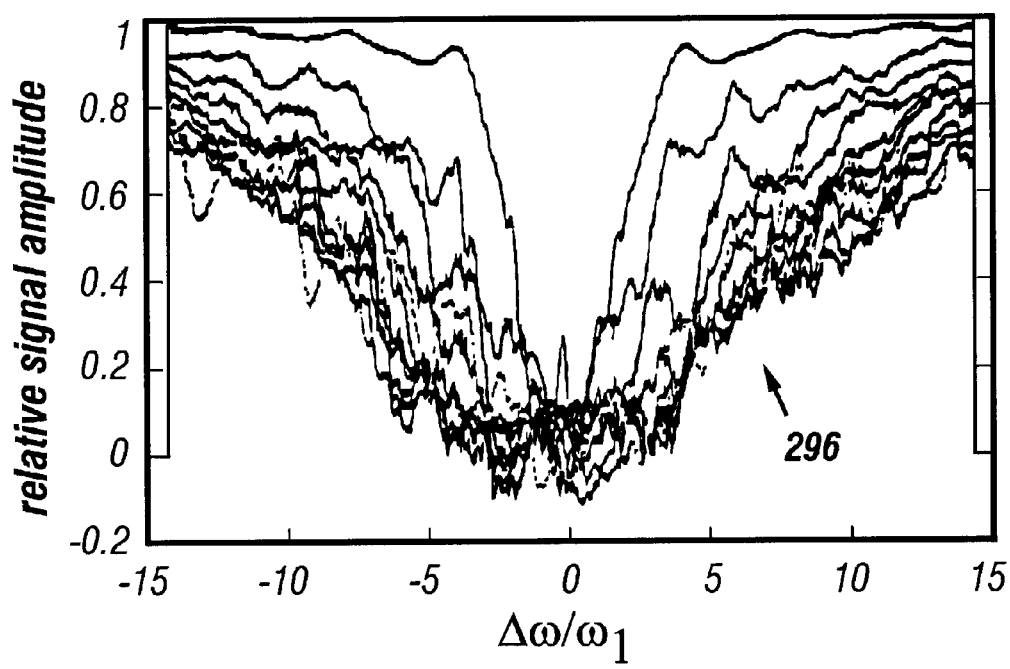

This effect is illustrated in FIG. 38 (showing a contour plot 294 of relative signal losses for different echo numbers) and FIG. 39 (showing plots 296 of relative signal losses for different echo numbers when averaged over a radial volume thickness of $\pm 0.75\omega_1$) for the example of slowly increasing pulse length (denoted "$t_p$" in FIG. 30). In this simulation, the pulse length was increased linearly from 125 $\mu$s (a 180° pulse) for the first refocusing pulse to 250 $\mu$s (a 360° pulse) for the 100th refocusing pulse while $t_{free}$ (the distance between pulses, as depicted in FIG. 30) was kept fixed. All other parameters are the same as in the previous example. The resulting saturation profile is smoother and slightly wider than without variation of the pulse length.

Also, in general, the saturation effect of the pulse sequence may be optimized for a particular range of motion by varying the various parameters of the sequence, like $t_e$, which is about inversely proportional to the separation of the burned holes, $t_p$, the pulse phases, etc. and trading off between coherent and stochastic features.

The previous examples of saturation sequences used the far-off-resonance hole burning effect to create saturation. As stated above, a pulse of duration $t_p$ rotates a spin that is off resonance through the angle $\alpha(\Delta\omega)$ that is always bigger than the nominal flip angle $\alpha(0)$. Therefore, for refocusing pulses with $\alpha(0)=180°$ (i.e., "180 degree pulses"), it always holds $\alpha(\Delta\omega)>180°$ far off resonance. On the other hand, optimal excitation and thus, optimal excitation off resonance occurs if $\alpha(\Delta\omega)=(2n+1)\cdot 180°$. Then the effective flip angle through which a spin is turned away from the longitudinal axis is $\theta=\theta_{max}$, with $$\theta_{max} = 2\arctan\left(\frac{\omega_1}{\Delta\omega}\right)$$

being the maximum effective flip angle for a given $\Delta\omega$. Therefore, using 180° pulses to create off resonance saturation may waste energy.

FIGS. 40 and 41 illustrate the dependence of the saturation profile (averaged over a resonance shell thickness) on $\alpha(0)$ of the refocusing pulses used in the sequence. The phases were varied stochastically as previously described. In FIG. 40, relative signal losses 298 are illustrated for the $t_{free}$ evolution time (i.e., the time interval between refocusing pulses, as illustrated in FIG. 30) being set to 375 $\mu$s, and in FIG. 41, relative signal losses 100 are illustrated for the $t_{free}$ time being set to zero. In both FIGS. 40 and 41, the signal losses 298 and 300 are illustrated for 1 to 100 pulses for the flip angles 9°, 20°, 30°, 45°, 90° and 180° as a function of $\Delta\omega$. The different flip angles are created by varying the $t_p$ pulse duration. As can be seen, the signal loss distributions are almost identical for different $t_{free}$, times, and thus, under stochastic phase variation, the saturation pattern is determined mainly by the pulse duration and not by the duration of the free evolution period.

The minimal pulse duration that may be used with a given hardware is determined by the rising time constant (called $t_r$) of the pulse. If $t_p<3t_r$, then the pulse does not reach the maximum $\omega_1$ before it is switched off and it rapidly becomes less effective when $t_p$ is reduced further. For a well logging NMR apparatus, a good estimate is $t_r=5 \ldots 30$ $\mu$s.

When $t_p$ decreases, the saturated region becomes broader. Of practical interest is mainly the region with $$|\Delta\omega| < \sqrt{\left(\frac{2\pi}{t_p}\right)^2 - \omega_1^2},$$

that is, the region with $\alpha(\Delta\omega)<2\pi$ within the two inner unsaturated nodes. The maximum flip angle $\alpha$ decreases with increasing $\Delta\omega$. Therefore, the wider the saturation region, the more pulses are needed to create saturation. If the time constant for saturation is $T_s$, then only spins with $T_1>T_s$ can be saturated fully. Therefore, a tradeoff may be made between saturation bandwidth and the lowest $T_1$ that still may be saturated. Also this shows that, in some embodiments, it is advantageous to keep the sequence as short as possible by minimizing $t_{free}$ to the lowest possible value that can be obtained with the available hardware.

FIGS. 42 and 43 illustrate the losses 302 and 304 for sequences with (FIG. 24) and without (FIG. 25) $t_{free}$, respectively. The losses 302 and 304 are shown for different relaxation times. With $t_{free}=375$ $\mu$s, the sequence of 100 refocusing pulses is 40 ms long, and without the free evolution period, the sequence is only 2,4 ms long. For a nominal flip angle $\alpha(0)=35°$, both sequences are capable of saturating spins with relaxation times of free fluid (T1>50 ms), but the sequence without free evolution period is capable of saturating spins with 20 times lower $T_1$, which is needed if one wants to resolve spin distributions below the bound fluid cutoff. In both cases, the energy needed to create the saturation is $$100\frac{35}{180} \approx 20$$

times the energy for a single 180° refocusing pulse, an energy that should pose no serious problem for downhole NMR tools that usually are able to create trains of hundreds of 180° refocusing pulses out of energy stored in capacitors during $t_w$.

In some embodiments, the profiles burned with sequences that include a free evolution period are somewhat smoother than the patterns burned by continuous irradiation. This might stem from additional dephasing that occurs during the free evolution period that is missing in the second case, but is not critical. In addition, if a tool with axisymmetric field geometries is displaced by the distance $\vec{\Delta r}$, every spin, depending on its position on the azimuth, experiences a different displacement in frequency space $\Delta\omega = d\omega_0/d\vec{r} \cdot \vec{\Delta r}$. This leads to an additional effective smoothing of the actual saturation profile.

In the simulations described above, the four pulse phases were chosen using a random number generator. Therefore, the performance of a sequence varies slightly from sequence to sequence, and in some embodiments, a predetermined sequence of phases might be used to optimize the saturation performance. In some embodiments, an optimal parameter variation may be one without periodicity.

II. Use of Motion Sensors to Detect and Characterize Tool Motion for Correcting and Checking the Quality of NMR Measurements If the tool motion is known, the NMR response of the tool may be simulated numerically, and within limits, motion-distorted measured data may be corrected using, for example, three types of motion detection devices: accelerometers, strain gauges and magnetometers. Other types of motion detection devices are also possible, such as ultrasonic sensors, for example. The motion detection devices may be part of the circuitry 42 (see FIG. 8, for example) of the tool or tool unit.

The magnetometers record the instantaneous orientation and thus, record the time-resolved rotation of the tool. This information is used to aid the other measurements. For example, the magnetometers may be used to rotate measured quantities of the other sensors into an earth-fixed frame of reference to the accelerometers. Magnetometers may be used to subtract out the acceleration component that is caused by rotation of the tool.

Accelerometers may be used to describe the characteristics of the pathway the tool is taking by the following technique: a. repeatedly filtering the data (e.g., to take out DC offsets, low-frequency numerical and drift noise and high-frequency noise unrelated to macroscopic collar motion); b. integrating the acceleration data once to yield a velocity trajectory in time; and c. integrating the data again to yield a position trajectory in time. The integration constants are chosen in accordance with useful physical assumptions, such as that the average displacements and velocities over a long enough time period are zero. Useful information that may be distilled out of the measurements from the accelerometer(s) may include information about motion amplitudes; average motion radius; motion frequency; histograms of position, velocity and acceleration; shock logging and characterization; and shock statistics. In some embodiments, a pair of accelerometers may be mounted on opposite sides of the tool. In this manner, the sensitive axes of the pair of accelerometers are oriented in the same direction so that the sum of the indicated accelerations may be used to derive the rotation of the tool and the difference of the indicated accelerations may be used to derive the translation of the tool.

Strain gauges directly measure the bending of the drilling tool. The strain gauges may be, as examples, located in the drill collar or on the chassis inside the collar. The bending of the drilling tool is related to lateral displacement of the collar section that may contain the strain gauges. Thus, the strain gauges measure, albeit with an unknown scaling factor, the same displacement trajectory that can be inferred from the accelerometers only after doubly integrating. Therefore, the strain gauges may be used to dynamically adapt the accelerometer's data integration. For example, one such technique includes identifying the points with zero velocity and position and continuously adjusting the acceleration integration based on this data. Another technique is to use the accelerometers to determine motion amplitudes and strain gauges to determine motion frequencies.

Especially in the case of the low gradient motion and large-amplitude motion that starts to interfere even with T1-based methods, the sensitivity of the above-described sensors is sufficient to characterize the motion and thus, serve as a quality control flag for the NMR measurements. The data derived from one or more of the sensors may also be used to correct the echo amplitudes.

While the invention has been disclosed with respect to a limited number of embodiments, those skilled in the art, having the benefit of this disclosure, will appreciate numerous modifications and variations therefrom. It is intended that the appended claims cover all such modifications and variations as fall within the true spirit and scope of the invention.

What is claimed is:

1. A method usable with an NMR measurement apparatus, comprising:
   performing a plurality of NMR measurements of an earth formation sample, each measurement comprising a plurality of spin echoes, at least two of the measurements having different sensitivities to a motion of the apparatus with respect to the sample;
   detecting the plurality of spin echoes for each NMR measurement;
   comparing the spin echoes to detect the motion of the apparatus that occurred during at least one of the measurements.

2. The method of claim 1, wherein when motion is detected further comprising:
   determining an effect of the apparatus motion on at least one of the measurements based on the spin echoes.

3. The method of claim 2, further comprising using the effect to interpret at least one of the measurements.

4. The method of claim 2, further comprising using the effect to interpret at least one future measurement.

5. The method of claim 2, further comprising using the effect to interpret at least one past measurement.

6. The method of claim 2, further comprising using the effect to adjust a tool acquisition mode to compensate for the motion of the tool.

7. The method of claim 2, further comprising using the effect to adjust measurement data to compensate for the motion of the tool.

8. The method of claim 1, further comprising:
   using a first static magnetic field to conduct one of the NMR measurements and a second static magnetic field to conduct another one of the NMR measurements.

9. The method of claim 8, wherein said first magnetic field has a different field geometry than said second magnetic field.

10. The method of claim 8, wherein said first magnetic field has a different gradient than said second magnetic field and wherein apparatus motion is detected based on a ratio of the first and second gradients.

11. The method of claim 1, further comprising:
    radiating a first sequence of RF pulses to perform one of the measurements; and
    radiating a second sequence RF pulses to perform another one of the measurements.

12. The method of claim 11, wherein at least some of the pulses of the first sequence have a different magnitude than corresponding pulses of the second sequence.

13. The method of claim 11, wherein at least some of the pulses of the first sequence have a different duration than corresponding pulses of the second sequence.

14. The method of claim 11, wherein adjacent pulses of the first sequence are spaced further apart in time than corresponding adjacent pulses of the second sequence.

15. The method of claim 1, further comprising:
    using different types of pulse sequences to perform the measurements, the different types having different sensitivities to the motion.

16. The method of claim 1, further comprising:
    using a motion detection device to indicate the motion; and
    further basing the determination of the effect on the indication from the motion detection device.

17. The method of claim 1, wherein the using step comprises comparing measurements of a formation characteristic.

18. The method of claim 17, wherein the characteristic comprises a porosity.

19. The method of claim 17, wherein the characteristic comprises a bound fluid volume.

20. A method usable with an NMR measurement apparatus, comprising:
performing a plurality of NMR measurements of an earth formation sample to measure spin-spin relaxation times of the sample and to measure spin-lattice relation times of the sample, each measurement comprising a plurality of spin echoes, the spin echoes associated with the spin-spin relaxation times and the spin echoes associated with the spin-lattice relaxation times having different sensitivities to a motion of the apparatus with respect to the sample;
detecting the plurality of spin echoes for each NMR measurement;
comparing the spin echoes received in response to the spin-spin measurement with the spin echoes received in response to the spin-lattice measurement to detect the motion of the apparatus that occurred during at least one of the measurements.

21. The method of claim 20, wherein when motion is detected further comprising:
determining an effect of the apparatus notion on at least one of the measurements based on the spin echoes.

22. The method of claim 21, further comprising using the effect to interpret at least one of the measurements.

23. The method of claim 21, further comprising using the effect to interpret at least one future measurement.

24. The method of claim 20, further comprising:
using a motion detection device to indicate the motion; and
further basing the determination of the effect on the indication from the motion detection device.

25. The method of claim 20, wherein the using step comprises comparing measurements of a formation characteristic.

26. The method of claim 25, wherein the characteristic comprises a porosity.

27. The method of claim 20, wherein the characteristic comprises a bound fluid volume.

28. A method usable with an NMR measurement apparatus potentially subject to relative motion between the apparatus and a sample, the method comprising:
saturating spins in at least a first and second regions of an earth formation;
performing a plurality of NMR measurements of a characteristic of the regions, each measurement comprising a plurality of spin echoes, the spin echoes associated with the first region and the spin echoes associated with the second region having different sensitivities to a motion of the apparatus with respect to the sample;
detecting the plurality of spin echoes for each NMR measurement;
comparing the spin echoes received in response to measurements made in the first region with the spin echoes received in response to measurements made in the second region to detect the motion of the apparatus that occurred during at least one of the measurements.

29. The method of claim 28, wherein when motion is detected further comprising:
determining an effect of the apparatus motion on at least one of the measurements based on the spin echoes.

30. The method of claim 29, further comprising using the effect to interpret at least one of the measurements.

31. The method of claim 29, further comprising using the effect to interpret at least one future measurement.

32. The method of claim 29, further comprising using the effect to interpret at least one past measurement.

33. The method of claim 29, wherein the act of basing future measurements on the determination comprises measuring a bound fluid volume using a fixed T2 cutoff when the motion effect permits a long echo train measurement.

34. The method of claim 29, wherein the act of basing future measurements on the determination comprises measuring a bound fluid volume with a tapered T2 cutoff when the motion effect permits only a short echo train measurement.

35. The method of claim 29, wherein the act of basing future measurements on the determination comprises measuring a bound fluid volume using a T1-based measurement when the motion effect permits a long echo train measurement.

36. The method of claim 29, further comprising:
using a motion detection device to indicate the motion; and
further basing the determination of the effect on the indication from the motion detection device.

37. The method of claim 28, wherein one of the measurements comprises a T2-based measurement.

38. The method of claim 28, wherein the characteristics comprise initial amplitudes.

39. The method of claim 28, wherein the characteristics comprise porosity indicators.

40. The method of claim 28, wherein the act of comparing comprises determining if the ratio of two of the measurements exceeds a predefined threshold.

41. The method of claim 28, wherein the act of comparing comprises determining if the ratio of values of two of the measurements exceeds a predefined threshold.

42. A method usable with an NMR measurement, comprising:
performing a plurality of NMR measurements to produce at least a first set and second set of spin echo signals from an earth formation sample, the first set of spin echo signals and the second set or spin echo signals each having a sensitivity to a relative motion of the apparatus with respect to the sample; and
comparing a characteristic of the first set of echo signals with a characteristic of the second set of spin echo signals to detect the relative motion of the apparatus that occurred during at least one or the measurements.

43. The method of claim 42, wherein when motion is detected further comprising:
determining an effect of the apparatus motion on at least one of the measurements based on the spine echoes.

44. The method of claim 43, further comprising using the effect to interpret at least one of the measurements.

45. The method of claim 43, further comprising using the effect to interpret at least one future measurement.

46. The method of claim 43, further comprising using the effect to interpret at least one past measurement.

47. The method of claim 42, wherein the characteristic comprises an envelope shape of the signal.

48. The method of claim 42, wherein the characteristic comprises a frequency content of the signal.

49. The method of claim 42, wherein the act of analyzing comprises:
using a broadband filter to filter said at least one of the signals; and
using another filter matched to the expected shape of said at least one of the signals to filter said at least one of the signals.

50. The method of claim 42, wherein the act of analyzing comprises: using a filter adapted to provide an output signal that increases with magnitude as motion increases.

51. The method of claim 42, wherein the act of analyzing comprises:
filtering said at least one spin echo signal using different filters that have different motion characteristics; and
using the results of the filtering to generate the indication.

52. The method of claim 51, wherein the act of using comprises:
analyzing an absorptive component produced by one of the filters.

53. The method of claim 51, wherein the act of using comprises:
analyzing a dispersive absorptive component produced by one of the filters.

54. The method of claim 42, further comprising:
using a motion detection device to indicate the motion; and
further basing the analysis on the indication from the motion detection device.

55. The method of claim 42, wherein the step of using the results comprises
computing magnitudes of the signals before stacking the magnitudes.

56. The method of claim 55, wherein the step of stacking comprises stacking signals adjacent echo signals.

57. The method of claim 55, wherein the step of stacking comprises stacking antisymmetric magnitudes of the signals.

58. An NMR measurement apparatus potentially subject to relative motion between the apparatus and a simple, comprising
at least one magnet;
at least one coil; and
circuitry coupled to said at least one coil and adapted to use said at least one magnet and said at least one coil to:
perform a plurality of NMR measurements of an earth formation simple, each measurement comprising a plurality of spin echoes, wherein at least two of the measurements have different sensitivities to a motion of the apparatus with respect to the sample:
detect the plurality of spin echoes; and
compare the spin echoes to detect the motion between the apparatus and the sample that occurred during at least one of the measurements.

59. The NMR measurement apparatus of claim 58, wherein said at least one magnet comprises:
a first permanent magnet adapted to establish a first magnetic field to conduct one of the measurements; and
a second permanent magnet adapted to establish a second magnetic field to conduct another one of the measurements.

60. The NMR measurement apparatus of claim 59, wherein the first and second magnetic fields have different geometries.

61. The NMR measurement apparatus of claim 59, wherein the first and second magnetic fields have different gradient patterns.

62. The NMR measurement apparatus of claim 59, wherein the circuitry is further adapted to perform one of the measurements by radiating a first sequence of pulses and perform another one of the NMR measurements by radiating a second sequence of pulses.

63. The NMR measurement apparatus of claim 59, wherein at least some of the pulses of the first sequence have a larger magnitude than corresponding pulses of the second sequence.

64. The NMR measurement apparatus of claim 59, wherein adjacent pulses of the first sequence are spaced further apart in time than corresponding adjacent pulses of the second sequence.

65. The NMR measurement apparatus of claim 62, wherein the first sequence has a greater sensitivity to the motion than the second sequence.

66. An NMR measurement apparatus potentially subject to relative motion between the apparatus and a sample, comprising
at least one magnet;
at least one coil; and
circuitry coupled to said at least one coil and adapted to use said at least one magnet and said at least one coil to:
perform a plurality of NMR measurements of an earth formation sample to measure spin-spin relaxation times or the sample and to measure spin-lattice relaxation times of the sample, each measurement comprising a plurality of spin echoes, the spin echoes associated with the spin-spin relaxation times and the spin echoes associated with the spin-lattice relaxation times having different sensitivities to a motion of the apparatus with respect to the sample;
detect the plurality of spin echoes;
compare the spin echoes received in response to the spin-spin measurement with the spin echoes received in response to the spin-lattice measurement to detect that motion between the apparatus and the sample occurred during at least one of the measurements.

67. An NMR measurement apparatus potentially subject to relative motion between the apparatus and a sample, comprising
at least one magnet;
at least one coil; and
circuitry coupled to said at least one coil and adapted to use said at least one magnet and said at least one coil to:
saturate spins in at least a first and a second region of an earth formation;
perform a plurality of NMR measurements of characteristics of the first and second regions, each measurement comprising a plurality of spin echoes, the spin echoes associated with the first region and the spin echoes associated with the second region having different sensitivities to a motion of the apparatus with respect to the sample;
detect the plurality of spin echoes;
compare the spin echoes received in response to measurements made in the first region with the spin echoes received in response to measurements made in the second region to detect that motion between the apparatus and the sample occurred during at least one of the measurements.

68. The NMR measurement apparatus of claim 67, wherein at least one of the NMR measurements comprises a T2-based measurement.

\* \* \* \* \*